United States Patent
Keyes et al.

(10) Patent No.: US 11,892,406 B2
(45) Date of Patent: Feb. 6, 2024

(54) METHOD AND DEVICE FOR ASSAYING THE INTERACTION AND DYNAMICS OF PERMEATION OF A MOLECULE AND A LIPID BILAYER

(71) Applicant: DUBLIN CITY UNIVERSITY, Dublin (IE)

(72) Inventors: Tia Keyes, Dublin (IE); Rokas Sakalys, Dublin (IE); Kiang Wei Kho, Dublin (IE); Agata Steplewska, Dublin (IE); Aurelien Gimenez, Dublin (IE); Nirod Kumar Sarangi, Dublin (IE)

(73) Assignee: DUBLIN CITY UNIVERSITY, Dublin (IE)

( * ) Notice: Subject to any disclaimer, the term of this patent is extended or adjusted under 35 U.S.C. 154(b) by 0 days.

(21) Appl. No.: 16/973,557

(22) PCT Filed: Jun. 7, 2019

(86) PCT No.: PCT/EP2019/065044
§ 371 (c)(1),
(2) Date: Dec. 9, 2020

(87) PCT Pub. No.: WO2019/238589
PCT Pub. Date: Dec. 19, 2019

(65) Prior Publication Data
US 2021/0247314 A1    Aug. 12, 2021

(30) Foreign Application Priority Data
Jun. 11, 2018  (GB) .................... 1809527

(51) Int. Cl.
*G01N 21/64* (2006.01)
*B01L 3/00* (2006.01)
(Continued)

(52) U.S. Cl.
CPC ...... *G01N 21/648* (2013.01); *B01L 3/502707* (2013.01); *G01N 21/6408* (2013.01);
(Continued)

(58) Field of Classification Search
CPC ............ G01N 21/648; G01N 21/6408; G01N 21/658; G01N 33/48721; B01L 2300/0829
See application file for complete search history.

(56) References Cited

U.S. PATENT DOCUMENTS
2017/0176449 A1   6/2017 Keyes et al.

FOREIGN PATENT DOCUMENTS
WO    2016001391 A1    1/2016
WO    WO-2016001391 A1 *  1/2016  ......... G01N 21/658

OTHER PUBLICATIONS

Banerjee, A. et al. "Micro-fluidic channels on nanopatterned substrates: monitoring protein binding to lipid bilayers with surface enhanced Raman spectroscopy", 2010 Chem. Phys. Lett. 489 121-6 (Year: 2010).*

(Continued)

*Primary Examiner* — Tarifur R Chowdhury
*Assistant Examiner* — Roberto Fabian, Jr.
(74) *Attorney, Agent, or Firm* — NIXON PEABODY LLP; David S. Resnick; Nicole D. Kling

(57) ABSTRACT

A method of assaying the interaction of a molecule and a lipid bilayer is described. The method employs a microfluidic device comprising a substrate having at least one concave microcavity with a metallic surface defining an aperture and a liquid disposed within the microcavity, a lipid bilayer suspended across the aperture, and a microfluidic channel containing a liquid disposed on top of the substrate in fluid communication with the lipid bilayer. The method comprises the steps of passing a liquid containing a test (Continued)

molecule across the microfluidic channel, and monitoring lipid bilayer molecule interactions by plasmonically enhanced Raman or fluorescence spectroscopy configured for plasmonic enhancement of a detection signal evolving from the test molecule or lipid bilayer. Also described in a microfluidic device configured to perform the method of the invention.

18 Claims, 13 Drawing Sheets

(51) Int. Cl.
    *G01N 21/65*     (2006.01)
    *G01N 33/487*     (2006.01)
(52) U.S. Cl.
    CPC ..... *G01N 21/658* (2013.01); *G01N 33/48721* (2013.01); *B01L 2300/0829* (2013.01)

(56) References Cited

OTHER PUBLICATIONS

Heywang, C. et al. "Orientation of anthracyclines in lipid monolayers and planar asymmetrical bilayers: a surface-enhanced resonance Raman scattering study", Biophys. J. 75 (1998), 2368-2381 (Year: 1998).*

Jung, S-Y et al. "Two-component membrane lithography via lipid backfilling." Chemphyschem 2005; 6:423-6 (Year: 2005).*

Tian, S. et al. "Fabrication of a bowl-shaped silver cavity substrate for SERS-based immunoassay", Analyst, 2013, 138, 2604 (Year: 2013).*

Sawai, Y. et al. "Photo-induced Metal Deposition onto a Au Electrode in Solution." J. Photochem. Photobiol., A 2003, 160, 19-25 ( Year: 2003).*

Heywang, Ch, et al. "SERR study of the interaction of anthracyclines with mono-and bilayers of charged phospholipids." Langmuir 13.21 (1997): 5634-5643. (Year: 1997).*

Banerjee et al., "Micro-fluidic channels on nanopatterned substrates: Monitoring protein binding to lipid bilayers with surface-enhanced Raman spectroscopy", Chemical Physics Letters 489 (2010) 121-126.

Basit et al., "Aqueous-filled polymer microcavity arrays: versatile & stable lipid bilayer platforms offering high lateral mobility to incorporated membrane proteins." Analyst 140.9 (2015): 3012-3018.

Jose et al., "Lipid bilayer assembly at a gold nanocavity array." Chemical Communications 47.46 (2011): 12530-12532.

Ramadurai et al., "Dynamic studies of the interaction of a pH responsive, amphiphilic polymer with a DOPC lipid membrane." Soft Matter 13.20 (2017): 3690-3700.

Slekiene et al., "Surface enhanced Raman spectroscopy of self-assembled layers of lipid molecules on hanostructured Au and Ag substrates." Chemistry and physics of lipids 203 (2017): 12-18.

Heywang et al. "SERR Study of the Interaction of Anthracyclines with Mono- and Bilayers of Charged Phospholipids." Langmuir, 13, 21, 5634-5643 (1997).

* cited by examiner

METHOD AND DEVICE FOR ASSAYING THE INTERACTION AND DYNAMICS OF PERMEATION OF A MOLECULE AND A LIPID BILAYER

CROSS-REFERENCE TO RELATED APPLICATIONS

This application is a 35 U.S.C. § 371 National Phase Entry Application of International Patent Application No. PCT/EP2019/065044 filed on Jun. 7, 2019, which designated the U.S., which claims benefit under 35 U.S.C. § 119(a) of GB Provisional Application No. 1809527.3 filed Jun. 11, 2018, the contents of which are incorporated herein by reference in their entireties.

FIELD OF THE INVENTION

The present invention relates to an assay method and device for assaying the interaction of a molecule or nanoparticle with a lipid bilayer and presence, residence time in and dynamics of permeation through said bilayer. Also contemplated are methods for fabricating sub-nanostructures on a substrate to promote sensitivity or selectivity in the assay.

BACKGROUND TO THE INVENTION

A key parameter in the pharmaceutical industry (which applies also across agrichemical and environmental and toxicological domains) is prediction of transmembrane (cell, plant prokaryotic or viral membrane) permeability of a given molecule or particle. In the pharma sector; many drugs have intracellular targets and thus transfer across the plasma membrane or intracellular membranes is required to elicit their response. Although it is widely asserted that cell membrane penetration by between 80 and 95% of commercial drugs is by passive diffusion there is much debate about the mechanism by which cells absorb drugs and other small molecules. (Current assessment of permeability as part of quantitative structure—activity relationship (QSAR) models are based on oil partitioning based parallel artificial membrane permeability assays (PAMPA) or cell based immobilised artificial membrane (IAM) approaches. The former is an inadequate model of the cell membrane, the latter, slow and expensive to implement. Although cell culture or in-vivo models are widely used to evaluate drug transport, both are time-consuming and expensive. Also, interpretation of results at a molecular level can be difficult because of the complexity of the cell and heterogeneity in cell populations. For example, where a drugs toxic effect originates from damage to membrane, such effects on membrane integrity are easier to identify in a model than a whole cell. There are currently no models available which give direct quantitative insight into permeation across through true phospholipid bilayers, dynamics of such interactions or that yield molecular level insights the interactions of molecules with the lipid bilayer.

WO2016/001391 describes a microfluidic device comprising a substrate having an array of concave microcavities with a metallic surface defining an aperture, a liquid disposed within the microcavity, a lipid bilayer suspended across the aperture, and a microfluidic channel containing a liquid disposed on top of the substrate in fluid communication with the lipid bilayer. WO2016/001391 also describes the use of the device to interrogate the lipid bilayer by electrochemical or fluorescence detection. The method is unable to provide any information on specific molecular interactions or lipid bilayer permeation data or permeation dynamics.

It is an object of the invention to overcome at least one of the above-referenced problems.

SUMMARY OF THE INVENTION

The present invention addresses the limitations of the prior art by providing a lipid bilayer substrate system, and assay method, that enables the simultaneous measurements of the test molecule-membrane interactions, and/or dynamics of permeation by monitoring the retention or residence time of the test molecule in lipid bilayer, arrival time of a test molecule within a cavity, or monitoring the lipid-bilayer. This is achieved through use of plasmonically enhanced spectroscopies (Raman or Fluorescent spectroscopy), that follow the intensity of Raman or fluorescent signal from test molecules (or particles) as they permeate through the bilayer and arrive at a plasmonic hots spot on the opposing side of the bilayer from where the molecule is administered, or by monitoring the lipid bilayer. This approach utilises the metal enhanced plasmonic fields (plasmons) generated in microcavities to monitor the transport and/or arrival of a test molecule based on detection of a plasmonic enhanced Raman or emission signal evolved from the test molecule or particle or lipid bilayer.

According to a first aspect of the present invention, there is provided a method of assaying the interaction of a molecule and a lipid bilayer that employs a microfluidic device comprising a substrate having at least one concave microcavity defining an aperture and having a metallic or partially metallic surface, and a liquid disposed within the microcavity, a lipid bilayer suspended across the aperture, and a microfluidic channel containing a liquid disposed on top of the substrate in fluid communication with the lipid bilayer. The method typically comprises the steps of passing a liquid containing a test molecule/particle across the microfluidic channel, and monitoring lipid bilayer molecule interactions by spectroscopy configured for plasmonic enhancement of a detection signal evolving from the test molecule or lipid bilayer (plasmonically enhanced Raman or fluorescent spectroscopy).

Also provided is a method of assaying the interaction of a test molecule and a lipid bilayer that employs a microfluidic device comprising:
- a substrate having at least one concave microcavity defining an aperture and having a metallic surface configured to generate a metal enhanced plasmonic field in the microcavity, and a liquid disposed within the microcavity;
- a lipid bilayer suspended across the aperture; and
- a microfluidic channel containing a liquid disposed on top of the substrate in fluid communication with the lipid bilayer, the method comprising the steps of:
- passing a liquid containing a test molecule across the microfluidic channel; and
- monitoring the transport and/or arrival of the test molecule by detection of a plasmonic enhanced Raman or emission signal evolved from the test molecule.

Also, provided is a method of assaying the interaction of a test molecule and a lipid bilayer that employs a microfluidic device comprising:
- a substrate having at least one concave microcavity defining an aperture with a metallic surface and a liquid disposed within the microcavity;

a lipid bilayer suspended across the aperture; and
a microfluidic channel containing a liquid disposed on top of the substrate in fluid communication with the lipid bilayer,
the method comprising the steps of:
passing a liquid containing a test molecule across the microfluidic channel; and
monitoring lipid bilayer-test molecule interactions by surface enhanced Raman spectroscopy (SERS), surface enhanced resonance Raman spectroscopy (SERRS), or metal enhanced fluorescence configured to monitor the intensity of a Raman or fluorescent signal from the test molecule as it permeates through the bilayer and/or arrives at a metal enhanced plasmonic field within the microcavity.

The use of metal microcavity to both capture a test molecule/particle after lipid bilayer transport, combined with plasmonically enhanced Raman or fluorescent spectroscopy to monitor and time transmembrane transport dynamics, provides a unique and elegant solution to the problems of the prior art systems and methods. The method of the invention allows monitoring through multi-modal detection strategies; Raman, FLCS and EIS, which can provide a breadth of information regarding the pharmacokinetics of drug and drug-membrane interactions.

The plasmonic enhanced spectroscopy employed in typically Raman Spectroscopy, or fluorescent spectroscopy. For fluorescent spectroscopy, the test molecule/particle must have some degree of fluorescence, although this can be very weak, or it can be labelled with a fluorescent label. The possibility to use Raman detection implies that fluorescent labelling can be avoided, thereby eliminating any confounding effect that might arise due to the label. Furthermore, the high-multiplexity of Raman spectroscopy means multiple analytes can be detected simultaneously in one single experiment.

The Raman spectroscopy may be selected from surface enhanced Raman spectroscopy (SERS) and surface enhanced resonance Raman spectroscopy (SERRS). Typically the exciting light must be coincident with the plasmon of the metal and in the latter case resonant to some degree with the absorption of the particle or molecule. The concave geometry of the microcavity permits modulation of the excitation field to excite different plasmonic modes, for example creating an in-cavity plasmonic hotspot, or a ring plasmonic mode around the aperture of the cavity, or employing different plasmonic modes. Thus, those localised at the bilayer or inside the cavity can be accessed by changing the excitation or detection angle of the incident light.

In one embodiment, the method includes a step of enhancing an electric field within the microcavity or around the aperture of the microcavity. This is achieved by providing a metal sub-nanostructure in the microcavity configured to focus the electrical field to the bottom of the well.

In one embodiment, the monitoring step comprises monitoring the retention time of the test molecule in the lipid bilayer.

In one embodiment, the monitoring step comprises monitoring arrival time of the molecule in the microcavity.

In one embodiment, the spectroscopy is fluorescence lifetime correlation spectroscopy.

In one embodiment, the molecule is fluorescent or comprises a fluorescent label.

In one embodiment, the monitoring step comprises monitoring arrival time or residence time of the molecule in the lipid bilayer.

In one embodiment, the monitoring step comprises changing the angle of excitation or collection of light. In one embodiment, the monitoring step employs large NA objectives to obtain a wide range of angles.

In one embodiment, the monitoring step comprises monitoring arrival time or residence time of the molecule in the lipid bilayer at a first excitation or detection angle of incident light, and then altering the excitation or detection angle of incident light to monitor arrival time of the molecule in the microcavity.

In one embodiment, the metallic surface of the microcavity comprises a sub-nanostructure configured to enhance a localised in-cavity plasmonic field.

The sub-nanostructure may be fabricated by a number of different methods, including direct photo-induced metal deposition to produce imprints of the plasmonic fields optionally near the bottom of the cavity, 3D-nanoprinting via 2-photon polymerization of photoresist, plasmonic field induced polymerization/metal deposition, air bubble excluded zone nanoparticle preparation, and reactive ion etching (RIF).

The test molecule may be a synthetic molecule such as a particle or a biological molecule. In one embodiment, the test molecule is a drug, toxin or agrochemical. In one embodiment, the test molecule is a vector for gene delivery, for example a liposome, nanoparticle or the like. In one embodiment, the test molecule is an active agent for cosmetic applications. The assay method of the invention may be used to assay drug delivery vehicles including nanoparticles, micro particles and liposomes and also may be used to assay toxiclogical effects of test molecules such as nanoparticles on membranes (e.g. in environmental applications).

In one embodiment, the metallic surface of or each microcavity is selected from gold or silver. The substrate may be formed from metal, or from a polymeric material. In one embodiment, the substrate is coated with metal. When gold is employed, the wavelength of the excitation line is configured to be coincident with the plasmonic absorption of the gold, and in the case of emission (fluorescence or phosphorescence) the excitation or the emission must be coincident with the energy of the plasmonic field for enhancement. Maximal plasmonic enhancement in these arrays depends on excitation and collection optics angles. In one embodiment, the metallic surface may be partially metallic, for example polymer plus metal. One example is an ostemer (polymer with localised regions of metal).

In another aspect, there is provided a substrate having at least one concave microcavity with a metallic surface defining an aperture, wherein the metallic surface of the at least one concave microcavity comprises a sub-nanostructure configured to enhance a localised in-cavity plasmonic field.

In one embodiment, the substrate comprises a plurality of concave microcavities comprising sub-nanostructures in an ordered array.

In one embodiment, one or each sub-nanostructures are fabricated by direct photo-induced metal deposition to produce imprints of the plasmonic fields optionally near the bottom of the cavity, 3D-nanoprinting via 2-photon polymerization of photoresist, plasmonic field induced polymerization/metal deposition, air bubble excluded zone nanoparticle preparation, or reactive ion etching (RIF).

In another aspect, the invention provides a microfluidic device comprising:
a substrate according to the invention;
a lipid bilayer suspended across the aperture of the at least one concave microcavity; and a microfluidic channel containing a liquid disposed on top of the substrate in fluid communication with the lipid bilayer of the at least one microcavity.

In one embodiment, the substrate comprises a plurality of concave microcavities comprising sub-nanostructures in an ordered array.

In another aspect, the invention provides a method of fabricating a substrate for a microfluidic device of the invention, the method comprising the steps of fabricating the at least one concave microcavity in the substrate, and subsequently fabricating a sub-nanostructure configured to enhance a localised in-cavity plasmonic field.

In one embodiment, the steps of fabricating a plurality of concave microcavity in the substrate, and subsequently fabricating a sub-nanostructure configured to enhance a localised in-cavity plasmonic field in each of the cavities in which the concave microcavities comprising sub-nanostructures are fabricated in an ordered array.

In one embodiment, the sub-nanostructure is fabricated by a method selected from the group consisting of:
direct photo-induced metal deposition to produce imprints of the plasmonic fields optionally near the bottom of the cavity;
3D-nanoprinting via 2-photon polymerization of photoresist;
plasmonic field induced polymerization/metal deposition;
air bubble excluded zone nanoparticle preparation; and
reactive ion etching (RIF).

In one embodiment, the at least one concave microcavity is fabricated by a method selected from the group consisting of: microsphere lithography; 3-D printing; and metal deposition.

In another aspect, there is provided a method of fabricating a microfluidic device according to the invention, comprising the steps of:
fabricating a substrate according to the invention or according to a method of the invention;
adding liquid to the at least one concave microcavity suspended a lipid bilayer across the aperture of the at least one concave microcavity; and
providing a microfluidic channel containing a liquid disposed on top of the substrate in fluid communication with the lipid bilayer of the at least one microcavity.

Other aspects and preferred embodiments of the invention are defined and described in the other claims set out below.

Inset shows the evolution of the fluorescent signal over time for the Doxorubicin administered to a DOPC bilayer.

Figure 12:
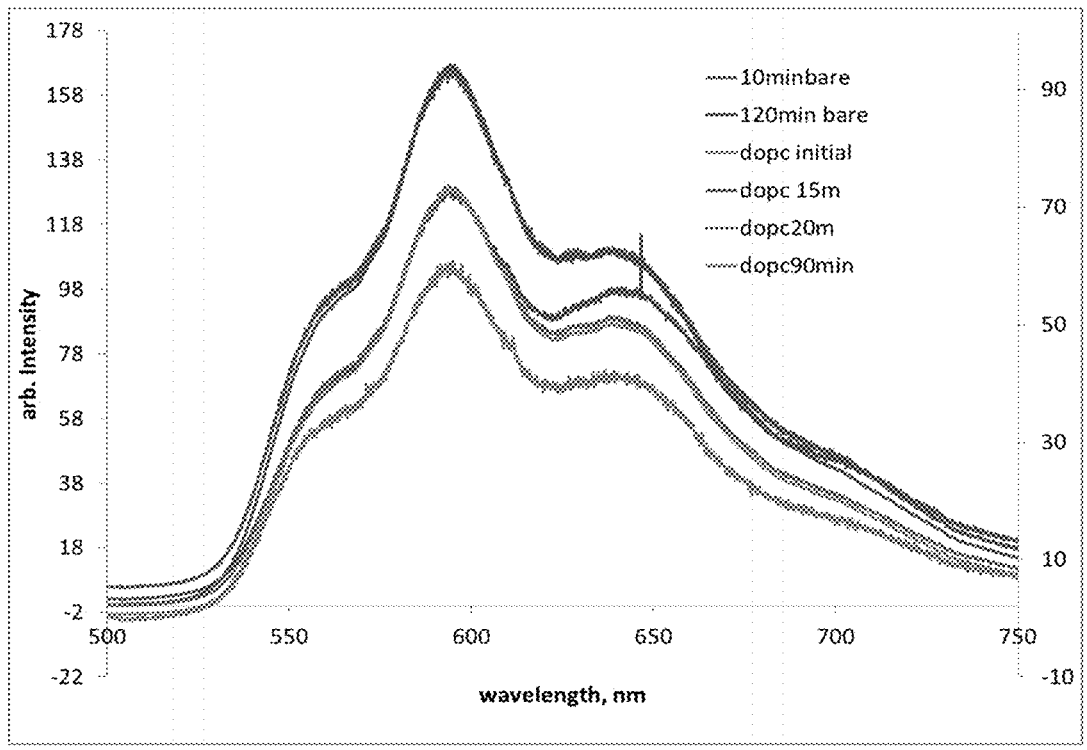

FIG. 12. Comparison of spectral changes as Doxorubicin diffuses into pores of unmodified cavity array compared to bilayer modified array. A transitory shift to the red in the peak in the vibrational progression occurs at 650 nm which is recovered at longer times when plasmonic enhanced solution signal from the pore dominates. By comparison there much negligible spectral changes to the compound in absence of bilayer other than intensity changes. (right axes). Spectra are normalized for clarity.

Figure 13:
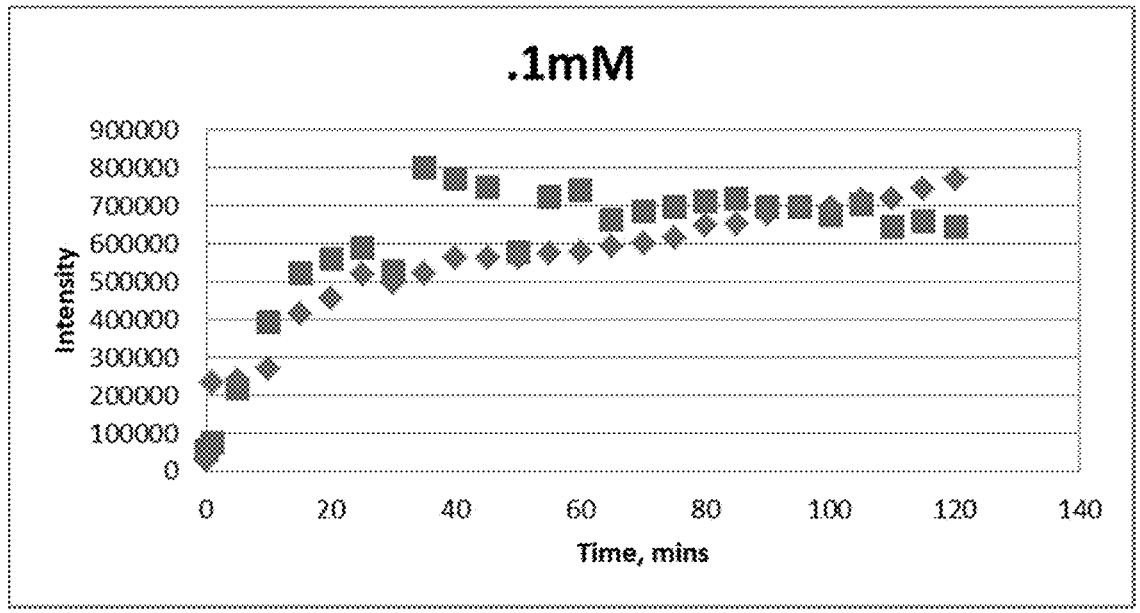

FIG. 13. Temporal intensity data for 0.1 mM Duanorubicin at gold microcavity array modified with a supported ternary domain forming lipid bilayer (DOPC:SM:Chol of 40:40:20% mol/mol). The data shown reflects two replicate measurements carried out on two different days/substrates. After an initial increase in intensity due to homogenization (the time scale of this step depends on the volume the drug is injected in to) of the drug in the contacting solution (and due to some MEF as the drug approaches the bilayer protected gold top surface of the array). In 2 mL contact solution, this process takes approximately 20 mins. The drug does not proceed to undergo the second intensity increase until it permeates the bilayer, this is observed as a semi-plateau region where emission intensity changes very slowly as the drug associates/assembles into the bilayer, the profile and time of this plateau period depends on both the drug (assuming it is permeable and on the bilayer composition). This period is followed by a dramatic increase in the emission intensity as the drug starts to escape the bilayer and diffuse into cavity, peaking as the drug distributes throughout the cavity. This dramatic intensity increase is influenced by the cavity plasmon and proceeds until equilibrium is reached and emission change plateaus. Where a drug is impermeable, the second emission rise and plateau is not observed. This was demonstrated for DRAQ7 and [Ru(bpy) 3[ complex, at DOPC bilayers. Both species are known to be membrane impermeable. For lower drug concentrations and complex, particularly domain-forming bilayer compositions permeation can be dramatically slower, ranging over many hours.

Figure 5:
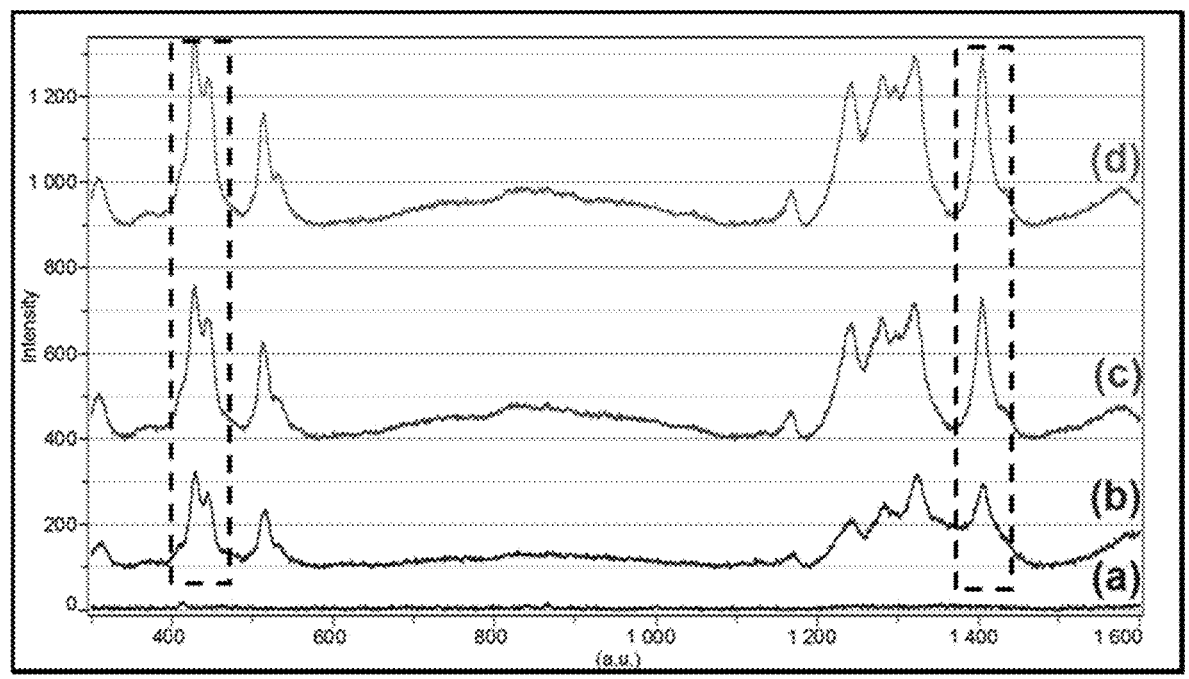
FIG. 5: SERS spectrum of DRAQ 7 far-red fluorescent dye solution of 5 μM: flat gold surface (a); cavities fabricated applying sphere lithography (b); cavities fabricated applying 3D printing based technology without nano gaps (c) and cavities fabricated applying 3D printing based technology with nano gaps (d)
Figure 8:
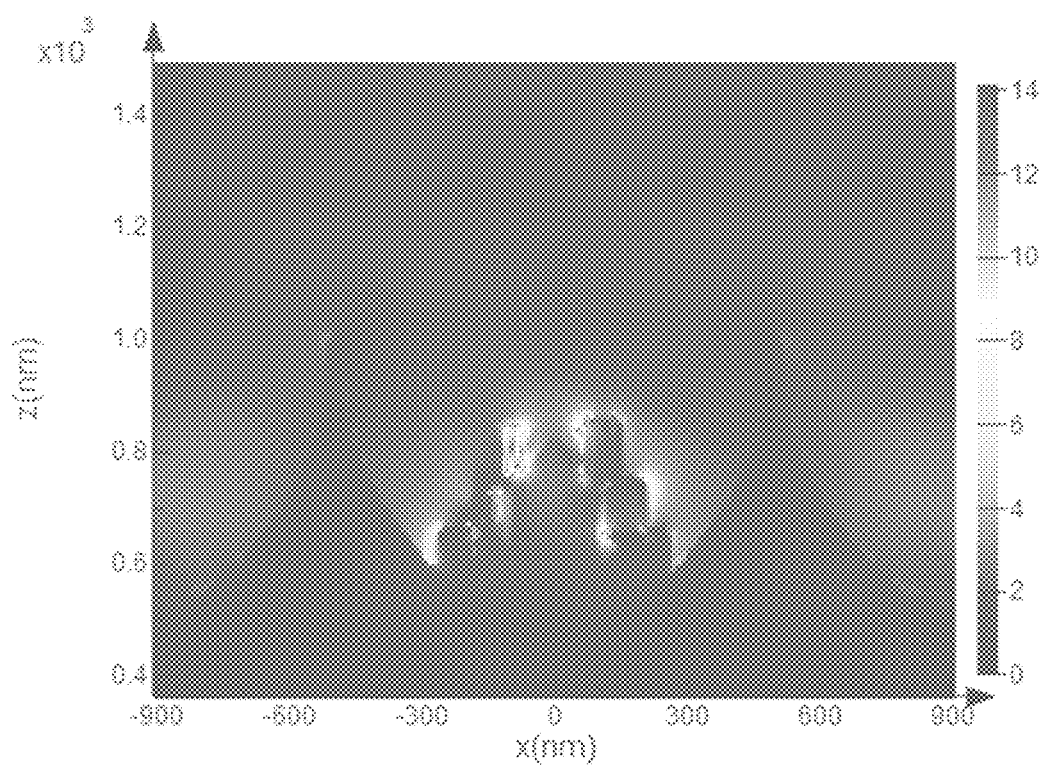
FIG. 8. (Left) In-cavity plasmonic fields excited with 0° illumination angle. (Right) Ring-plasmonic mode around the mouth of the cavities excited with 30° illumination angle.
Figure 8:
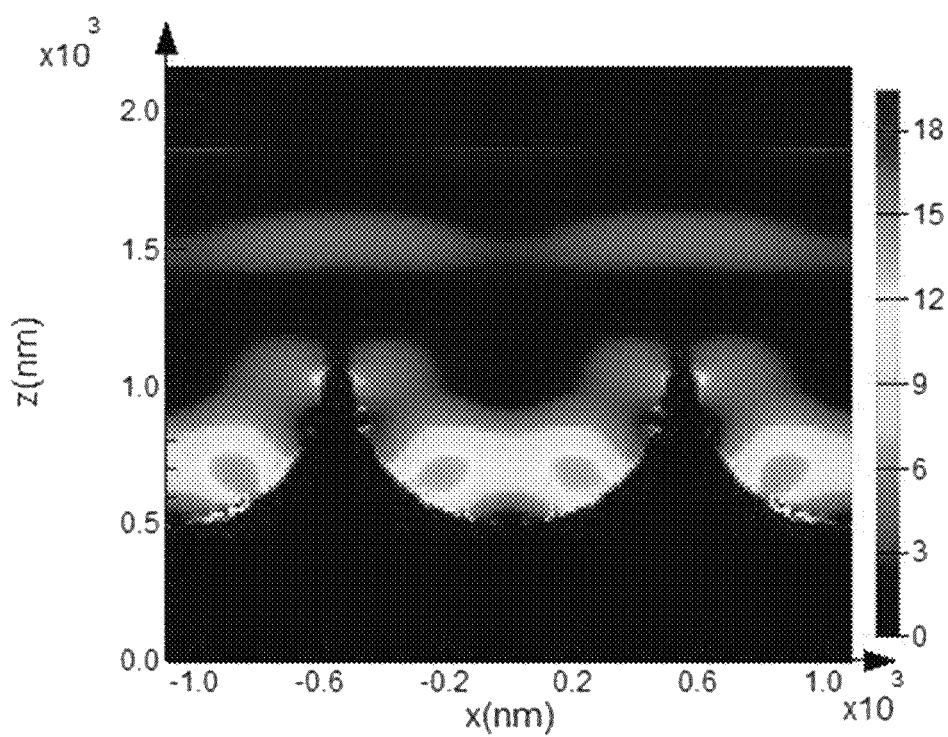
Figure 14:
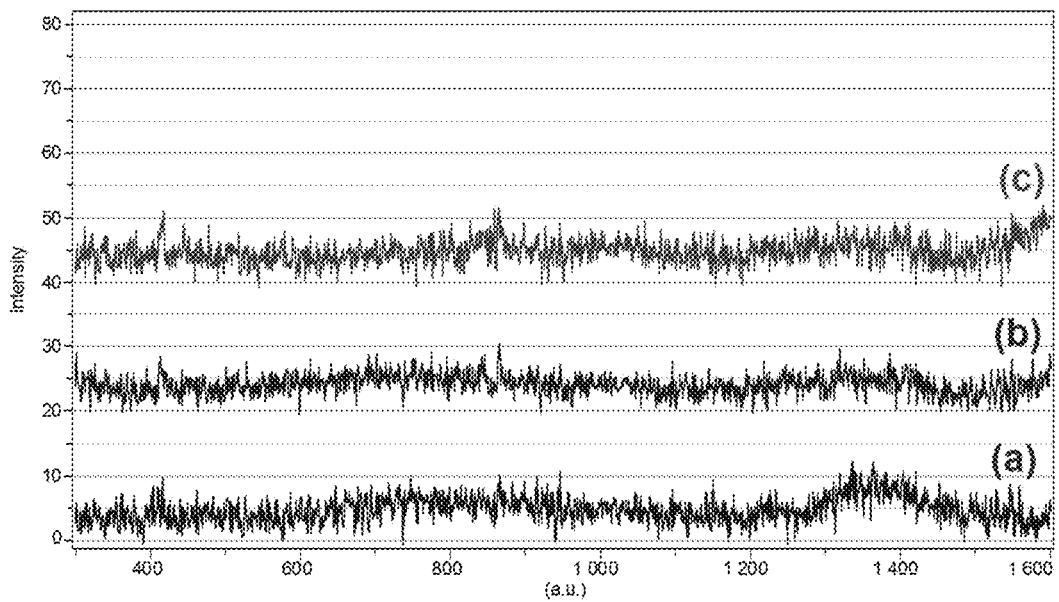

FIG. 14: shows the Raman spectra for DRAQ 7, a membrane impermeable probe when in contact with the 3-D printed nanostructured array described in FIG. 5, supporting a DOPC lipid bilayer. Weak Raman signal for the bilayer is observed but there is no evidence of DRAQ signal. FIG. 8 shows the grow in of the DRAQ 7 signal as the membrane is thermally permeabilized (in this case with laser). This data confirms that permeation can be followed by SERS enhancement of the drug analogue signal over time.

Figure 15:
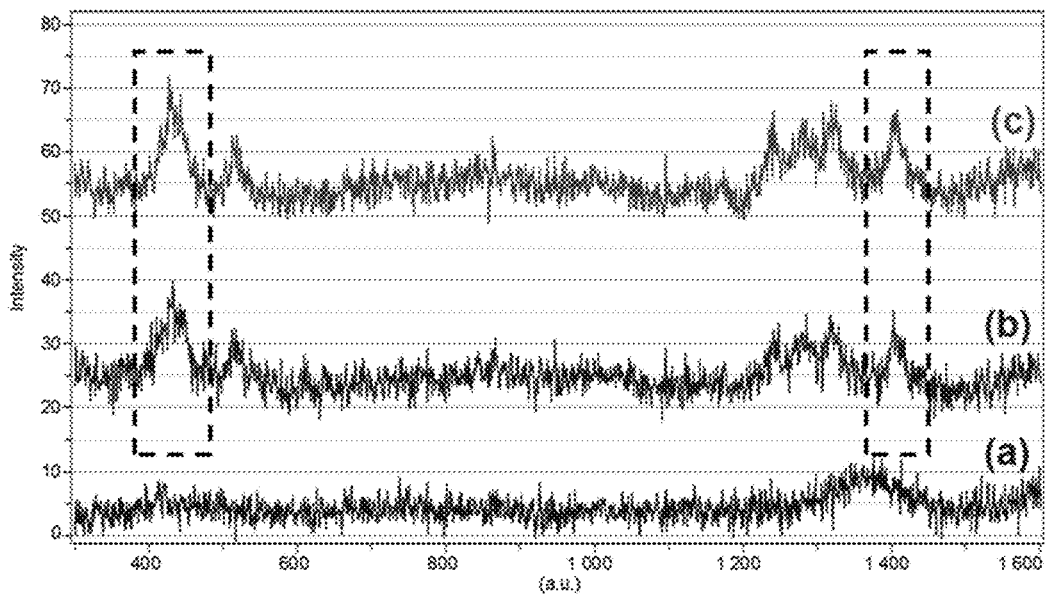

FIG. 15: SERS spectrum of DRAQ 7 far-red fluorescent dye solution of 10 μM after disruption of the DOPC lipid bilayer: flat gold surface (a); cavities without nano gaps (b) and cavities with nano gaps (c).

Figure 16:
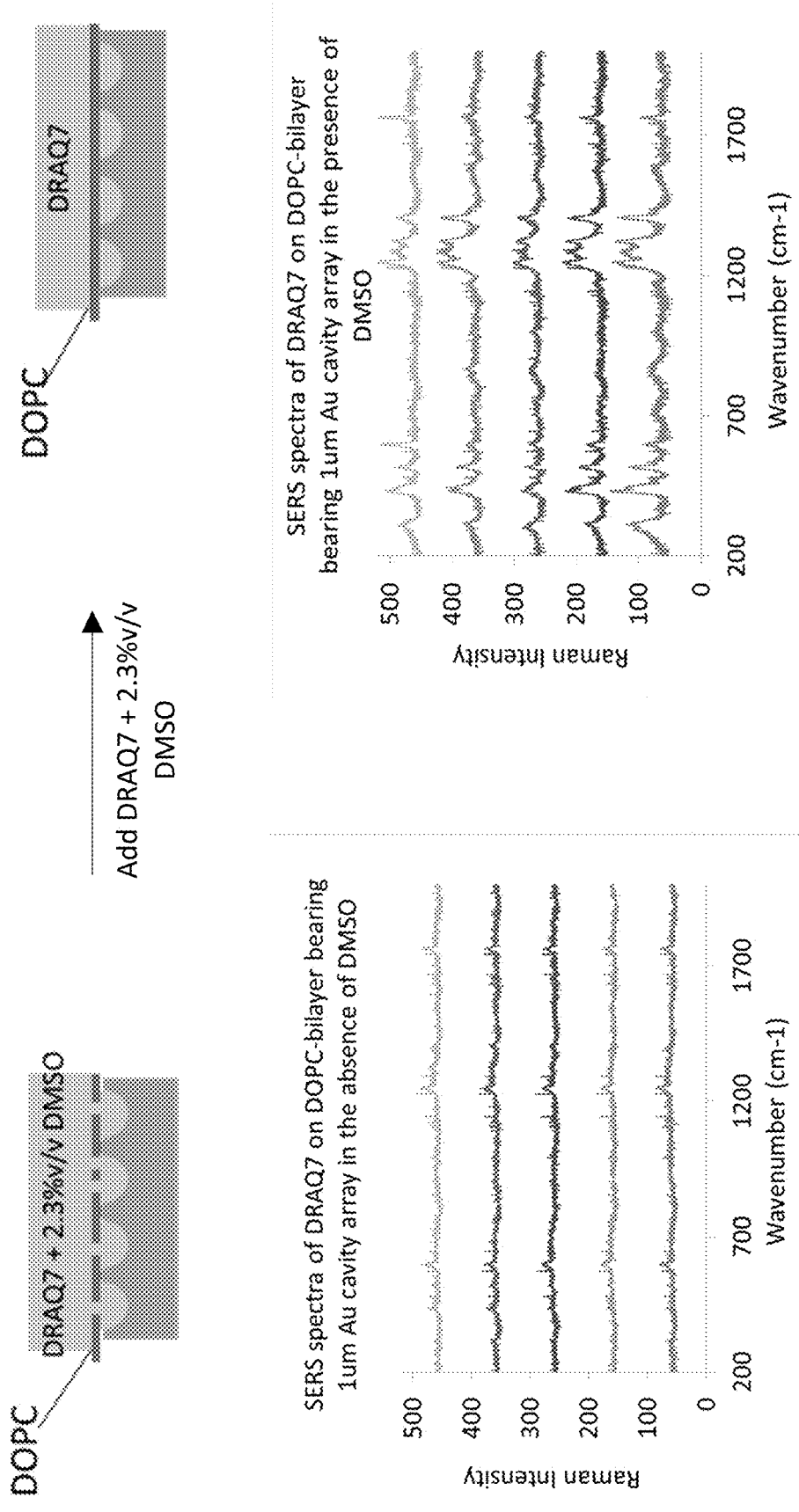

FIG. 16: shows an example of how the platform can be used to evaluate a permeabilization agent for membrane uptake. Here, left, only Raman features from the bilayer are evident when incubated with membrane impermeable DRAQ7. Following co-incubation with DMSO the DRAQ permeates the bilayer and SERS signal is evident as the drug analogue reaches the cavity.

Figure 17:
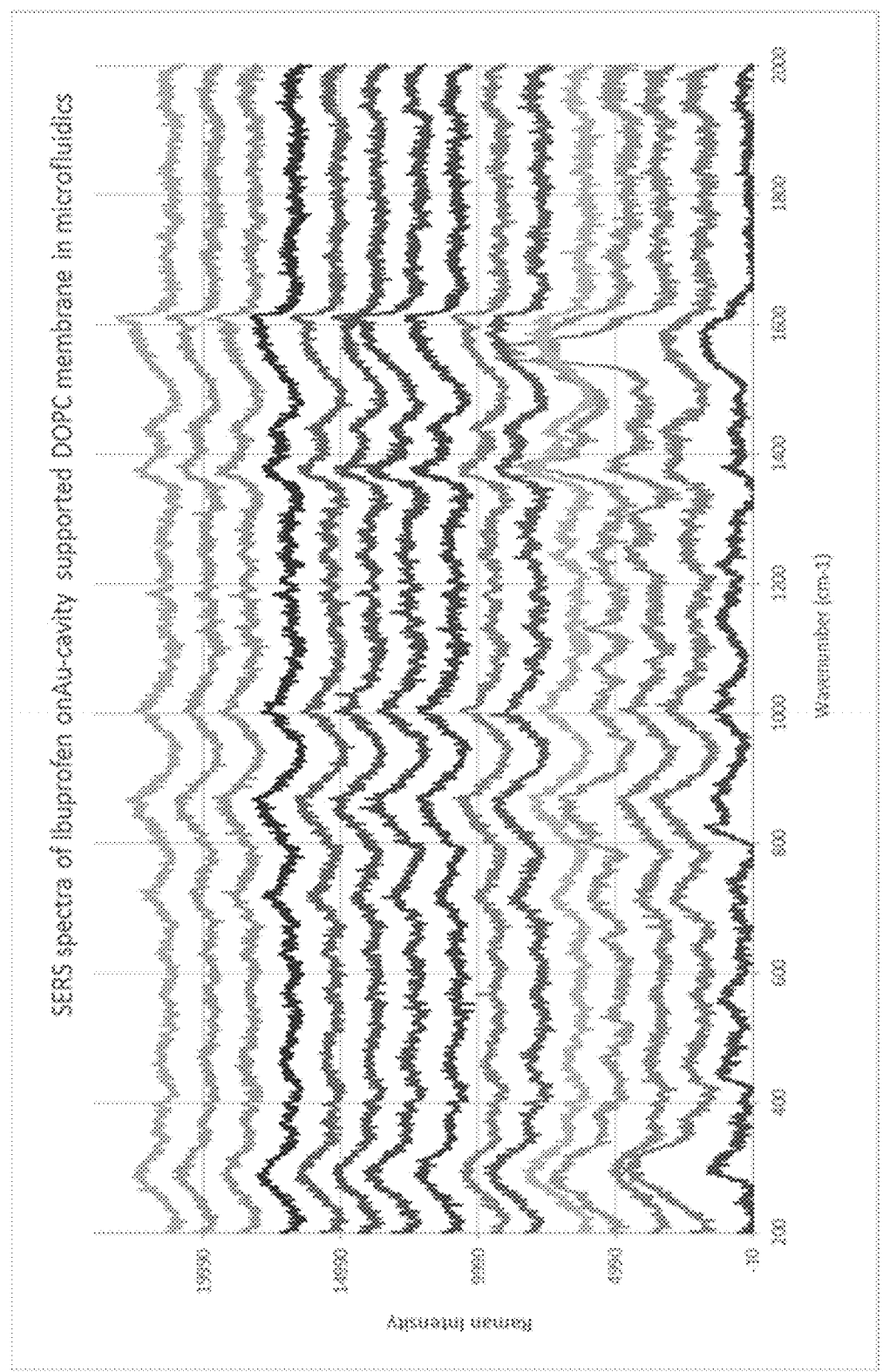

FIG. 17: Raman signal for 1 uMol Ibuprofen at DOPC bilayer assembled at 1 uM gold array in PBS buffer.

Figure 18:
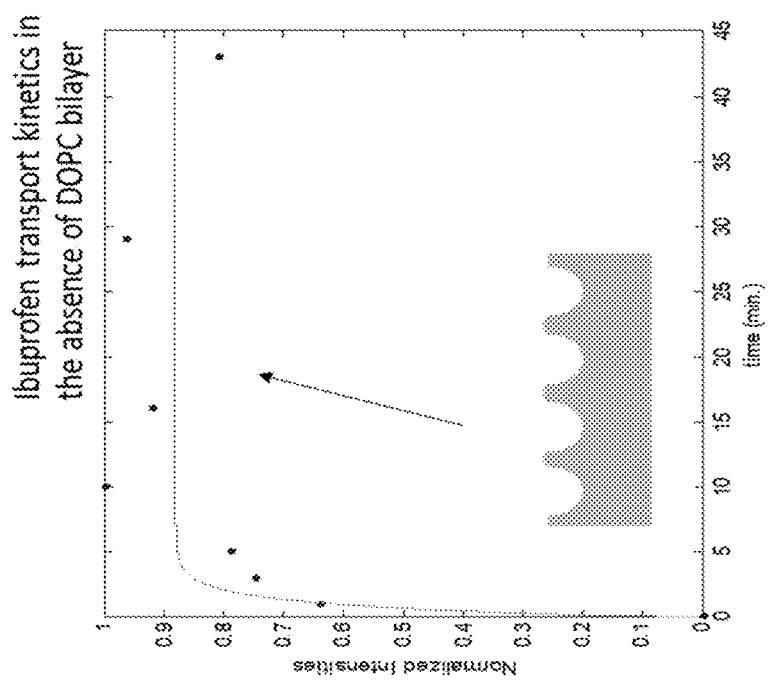
Figure 18:
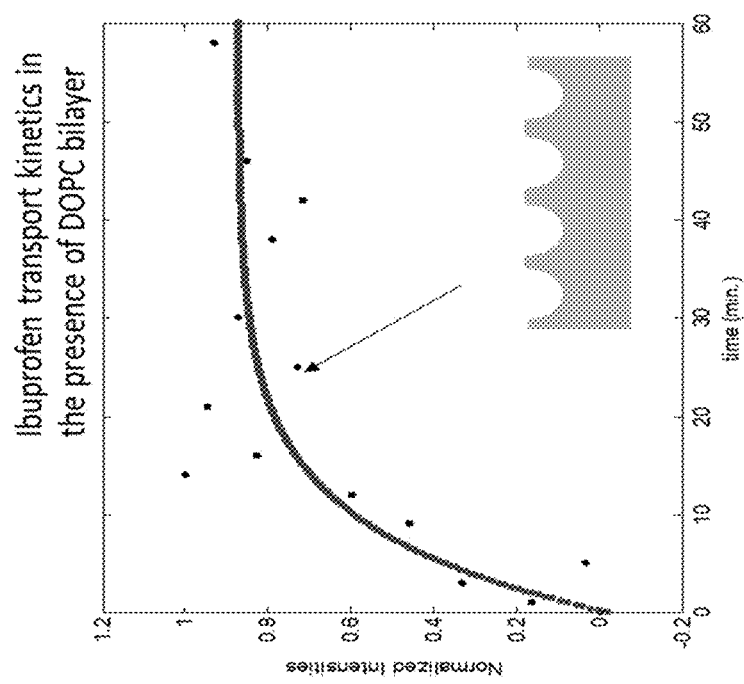

FIG. 18: the dynamics of evolution of the ibuprofen SERS signal in the presence and absence of bilayer. In presence of bilayer entrance to the cavity is slowed by the bilayer but it is passively permeable.

Figure 19:
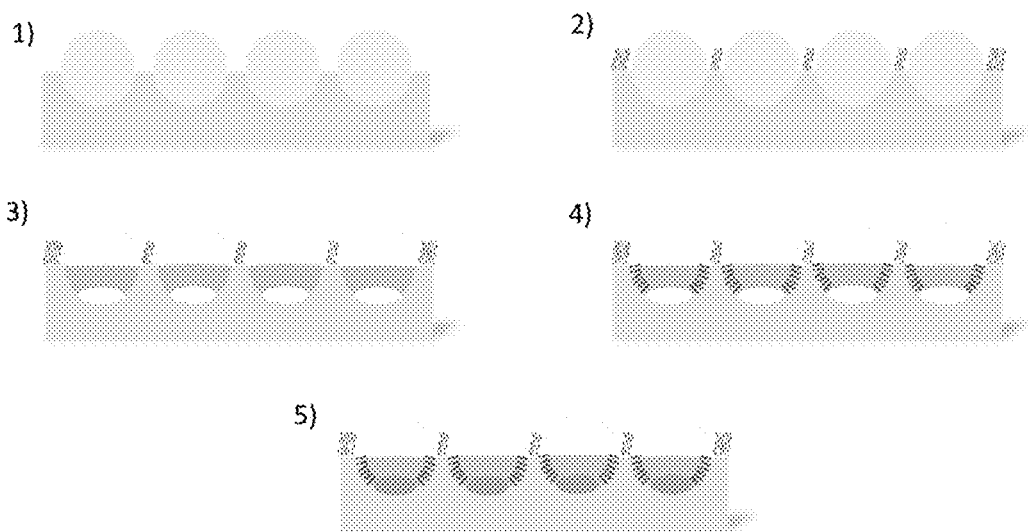

FIG. 19: Schematic showing steps in nanostructuring using the excluded volume of the thiol deposition solution.

Figure 20:
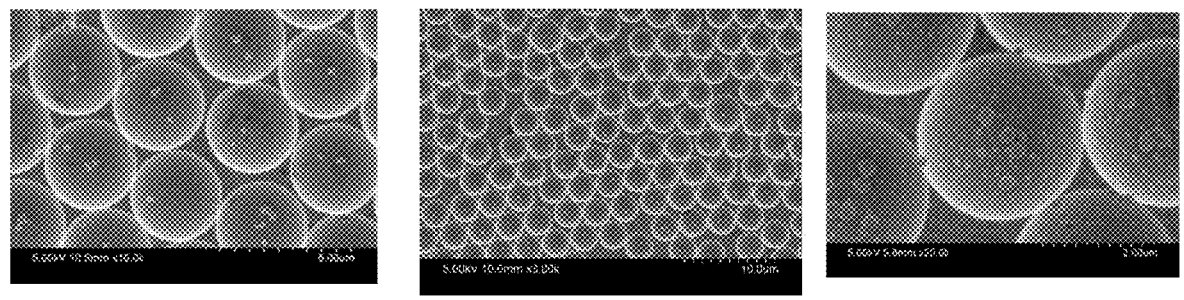

FIG. 20: nanoparticle modified arrays prepared from 3 um PS sphere assemblies after 30 seconds gold electrodeposition. (gold deposition left in contact with array left and middle and after prior sonication of gold deposition solution

DETAILED DESCRIPTION OF THE INVENTION

All publications, patents, patent applications and other references mentioned herein are hereby incorporated by reference in their entireties for all purposes as if each individual publication, patent or patent application were specifically and individually indicated to be incorporated by reference and the content thereof recited in full.

Definitions and General Preferences

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from infection, trauma, injury, surgery, radiological ablation, poisoning or nutritional deficiencies.

In the context of treatment and effective amounts as defined above, the term subject (which is to be read to include "individual", "animal", "patient" or "mammal" where context permits) defines any subject, particularly a mammalian subject, for whom treatment is indicated. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; and rodents such as mice, rats, hamsters and guinea pigs. In preferred embodiments, the subject is a human.

As used herein, the term "assaying the interaction of a molecule and a lipid bilayer" should be understood to cover one or more of assaying the residence or arrival time of the test molecule in the lipid bilayer, assaying the arrival time of the test molecule in the concave microcavity, assaying the transmembrane permeability of a test molecule (including whether the test molecule permeates the lipid bilayer, or whether it adsorbs without permeation at the membrane interface), how the permeation occurs, i.e. direct transport or via a transport protein, or assaying the permeation dynamics of the test molecule i.e. qualitative or quantitative), assaying whether the test molecule binds to the lipid bilayer, assaying whether the test molecule is toxic to the lipid bilayer, assaying the molecular-level interactions between impinging molecule and the lipid membrane structure (including phospholipid, sterol, glycolipid etc interactions) and impact of such interaction on the structure of the lipid and molecule. The term includes assessment of whether the drug/molecule can cross the membrane passively (as a function of bilayer composition), the dynamics of permeation across the membrane including molecule residence time at the membrane and arrival time on crossing (this can be assessed as a function of membrane composition, and assaying active transport of drug/molecule across suspended membranes reconstituted with protein.

As used herein, the term "molecule" should be understood to include a synthetic molecule or a biological molecule. In one embodiment, the test molecule is a drug, toxin, agrochemical, vector for gene delivery, virus, pharmaceutical excipient, an active agent of a cosmetic product. The molecule may be a protein, sugar, nucleic acid (i.e. oligonucleotide based therapeutic), antibody or antibody fragment, antibody-drug conjugate. The term encompasses low molecular weight compounds, and larger molecular structures (for example 4-10,000 KDa). It also includes particle structures such as liposomes, and nanoparticles.

As used herein, the term "lipid bilayer" refers to a thin semi-permeable membrane made of two layers of amphiphilic lipid molecules. While lipid bilayers exist in nature as cell membranes, the literature describes methods of making synthetic lipid including phospholipid and glycolipid bilayers, for example Pederson et al (Environ. Sci.: Nano, 2016, 3, 45 Formation of supported lipid bilayers containing phase-segregated domains and their interaction with gold nanoparticles) and Stanevac et al (Biochimica et Biophysica Acta (BBA)—Biomembranes Volume 1838, Issue 8, August 2014, Pages 2105-2114 Biochimica et Biophysica Acta (BBA)—Biomembranes Lo/Ld phase coexistence modulation induced by GM1) The lipid bilayer may be engineered to include one or more proteins. Methods of engineering lipid-protein bilayers are described in Keyes et al (Analyst. 2015 May 7; 140(9):3012-8. doi: 10.1039/c4an02317j. Epub 2015 Mar. 23. Aqueous-filled polymer microcavity arrays: versatile & stable lipid bilayer platforms offering high lateral mobility to incorporated membrane proteins). The lipid bilayer membrane can be a simple single phospholipid species such as DOPC or more complex ternary or beyond compositions that mimic true bilayers and can be selected to mimic disease or specific physiological organelles or tissues or indeed species such as bacteria.

As used herein, the term "substrate" refers to body of material in which the concave microcavities are formed. The substrate may be metal, or may be non-metal (for example a polymer) and may be coated with metal by any suitable means (for example electrochemical deposition). The concave microcavity generally has arcuate sidewalls and a maximum dimension of generally about 500 to 5000 microns, more preferably about 700-1200 microns. The aperture (across which the lipid bilayer is suspended) typically has a diameter of 500-1500 microns.

As used herein, the term "metallic surface" refers to a covering of a metal such as gold, silver, or another metal such as nickel, copper and platinum, or mixture of metals. The substrate may be formed from metal, or the metallic surface may be a coating of metal applied to the surface of the microcavities. Preferably, the substrate is polymer with a metallic coating. In one embodiment, the metallic surface may be partially metallic, for example polymer plus metal. One example is an ostemer (polymer with localised regions of metal).

As used herein, the term "liquid" as employed herein refers to a liquid that is capable of carrying the test molecule without damaging the molecule and without damaging the lipid bilayer. Generally, the liquid employed are aqueous in nature. The liquids above and below the lipid bilayer may be configured differently, to generate different gradients across the membrane, for example a pH, ionic, redox, or temperature gradient.

As used herein, the term "microfluidic channel" refers to a channel disposed above the substrate in fluidic contact with the lipid bilayers and configured to provide a flow of liquid containing a test molecule to the lipid bilayers. The microfluidic channel may be provided by a layer of material having microfluidic channels etched in a surface thereof that is placed upon the top of the substrate such that the microfluidic channel is in fluid communication with the lipid bilayers suspended on top of the cavities. Microfluidic channel and microfluidic devices suitable for us with the present invention are described in WO2016/001391.

Figure 1:
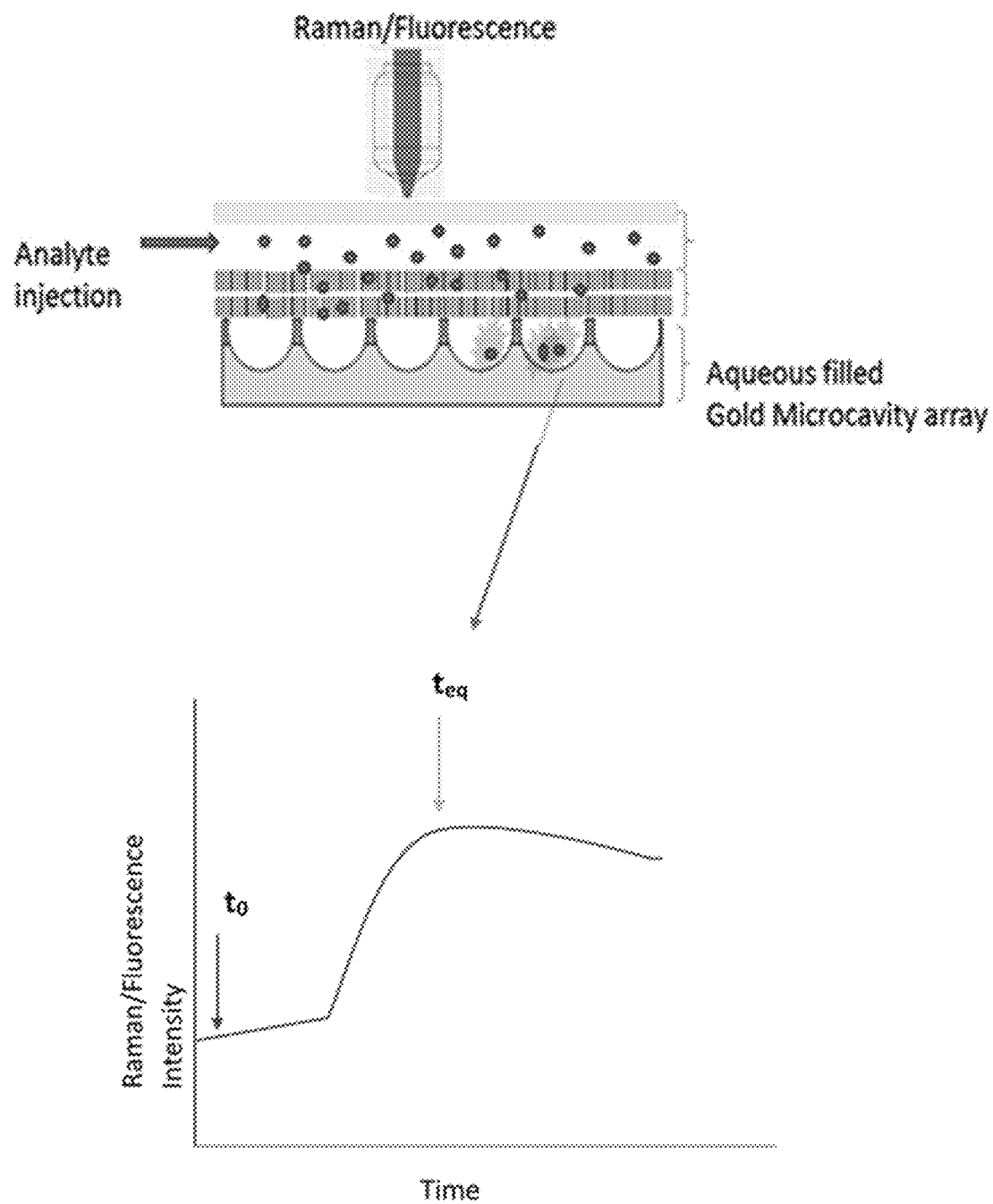
FIG. 1: illustration of concept behind membrane transport detection assay. Purple spots depict molecular or particle of interest.

As used herein, the term "spectroscopy configured for plasmonic or metal enhancement of a detection signal evolving from the test molecule" refers plasmonic enhanced Raman spectroscopy or plasmonic enhanced fluorescence spectroscopy. Enhancement is provided in the case of fluorescence by metal enhanced fluorescence which may arise from plasmonic promotion of excitation cross section, the radiative rate constant or through the focusing of the field within the cavity. Raman spectroscopy may be surface enhanced Raman spectroscopy (SERS) or surface enhanced resonance Raman spectroscopy (SERRS). For SERS, the exciting light typically must be coincident with the plasmon of the metal. For SERRS, the exciting light typically must be resonant to some degree with the absorption of the test molecule. In SERS, enhancement is achieved through excitation of the localised plasmon resonance of the cavity/surface. The location of the most intense electric field (plasmonic) may be controlled 1) by manipulation of excitation angle 2) by varying the material, nanostructuring (3) the excitation wavelength or 4) by controlling the focused field-structure via phase modulation. Thus, the bilayer itself can be monitored by metal (plasmonically and/or reflectance/Purcell effect) enhanced fluorescence or by surface enhanced Raman spectroscopy to study vibrational spectroscopy of drug-membrane binding, or the cavity interior can be monitored to identify permeation of the molecule (marked by arrival SERS or fluorescence signal) and to elucidate dynamics of diffusion across the membrane as a function of membrane composition, (lipid composition, presence of proteins or transporters) molecular (or particle concentration) or environmental conditions (pH, ionic strength). FIG. 1 above illustrates the principle.

As used herein, the term "metal sub-nanostructure" refers to a metallic structure formed on the surface of the concave microcavity having a sub-micron dimension that is configured to enhance a localised in-cavity plasmonic field typically by focusing the electric field towards a bottom of the microcavity. Plasmonically structuring the arrays through the incorporation of sub-nanostructures yields dramatically improved S/N of signal to interrogate the molecule by SERS or through use of surface enhanced resonance Raman spectroscopy (SERRS), where the excitation laser wavelength is matched to an electronic transition outstanding enhancement of Raman signature from non-luminescent species to can be investigated. Generally, the sub-nanostructure has a dimension of 5-200 nm. An example of a concave microcavity having a sub-nanostructure is shown in FIG. 5. Various methods for forming sub-nanostructures in concave microcavities are disclosed herein. For instance, direct photo-induced metal deposition may be employed to produce imprints of the plasmonic fields near the bottom of the cavity, thereby allowing for plasmonically-tagged drug arrival-time studies. Alternatively, 3D-nanoprinting via 2-photon polymerization of photoresist (e.g. acrylate photoresist) may be employed to produce customized sub-nanostructure within the cavity. These nano-structures may be computationally designed via, for instance, inverse algorithm.

Plasmonic field induced polymerization/metal deposition may be employed, where the plasmonic hots spot from the cavity array itself is used to deposit additional nanostructuring through direct metal photodeposition where cavities are filled with a metal salt solution or where a polymer solution filled in the cavity and photoinduced cross-linking driven by the plasmonic field is used to create insoluble polymer structures that can be deposited over with metal vapour deposition following washing to create hot spots.

Figure 2:
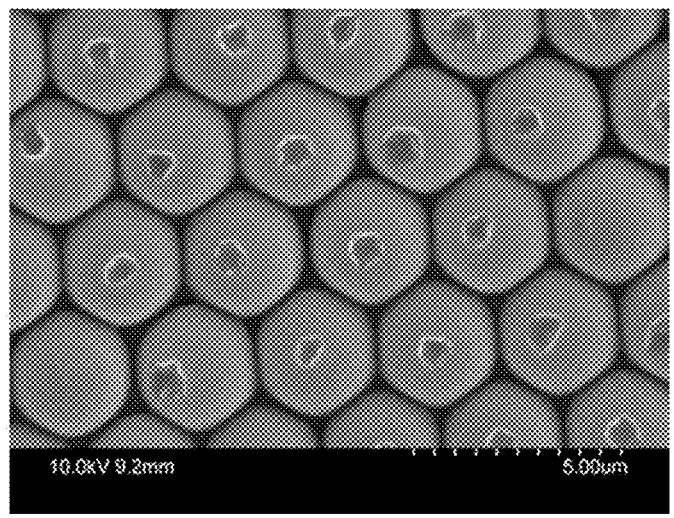
FIG. 2 SEM top view of PDMS positive structures cast from 3 μm diameter cavities formed by sphere deposition and filled without sonication. The image is highlighting the presence, size and position of air bubble in the cavities across the same substrate. This air bubble is exploited as a means of excluding thiol blocking at these positions and used as the points of deposition of metal nanostructure within the cavity.

Air bubble excluded zone nanoparticle prep (FIG. 2): Following filling by Fluorescence and SEM imaging of templated PDMS confirm that without sonication a small liquid unfilled region of the cavity is formed. We exploit this by, without sonication, filling Au cavity array pre-coated with C6 with an aqueous/ethanolic solution of surface active thiol. This blocks all but the region of the cavity where the air bubble is. Gold is then electrodeposited principally at the unmodified regions of the array to yield gold particles at the position of the air bubble in the well.

Fabrication of isolated Au-cavities with in-cavity nanostructures via reactive ion etching (RIF). In this approach, the cavities are prepared from electrodeposition of gold around PS sphere the spheres are then shrunk by RIF and a second (vapour) deposition is applied, this results in nanoflowers at the bottom of the well. FIG. 5 The resulting structures are highly uniform and the results once conditions of gold deposition are stable highly reproducible from batch to batch. Under normal incidence excitation/collection reproducible enhancement of SERS signature from these substrates is obtained compared to substrates without the additional nanostructuring (FIG. 5).

Exemplification

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

This application describes a highly versatile assay to determine the molecular interactions of molecules (e.g. drugs, agrichemicals or toxins) with biomimetic models of the cell membrane comprised of phospholipid bilayers supported across metal nanocavity arrays as model membranes.

The substrates provide electric field enhancement at discrete regions due to the Purcell effect, reflectance and/or localised surface plasmon located so that it is either coincident with the lipid bilayer and or below bilayer. Two types of platforms are described, conventional (plasmonic) metallic cavity arrays supporting lipid or lipid/protein bilayers and plasmonically enhanced arrays supporting lipid bilayers or lipid or lipid/protein where plasmonic hot spots within the arrays are augmented by implementation of additional nanostructures within the substrates to give spatially localised and augmented plasmonic enhancement of signal. The platforms may be used with normal incident angle excitation and collection of light or with angled incident and collection to achieve control over the region of study (bilayer or well).

Enhancement is provided in the case of fluorescence from by metal enhanced fluorescence which may arise from plasmonic promotion of excitation cross section, the radiative rate constant or through the focussing of the field within the cavity. In SERS enhancement, is achieved through excitation of the localised plasmon resonance of the cavity/surface. The location of the most intense electric field (plasmonic) may be controlled 1) by manipulation of excitation angle 2) by varying the material, nanostructuring (3) the excitation wavelength or 4) by controlling the focused field-structure via phase modulation.

FIG. 1 illustration of membrane transport detection. Illustration of the operation of the bilayer permeation assay PlasMem: The dynamics of molecular (e.g. drug) passive diffusion across the membrane suspended at a gold nanocavity array is followed through the evolving (surface enhanced) Raman or Fluorescence signal from the analyte which is enhanced as it reaches the plasmonic hot spot at the cavity interior after crossing the membrane. This provides a simple but quantitative indication of reagent permeation through the bilayer. Drug permeation/arrival time, drug membrane residence time and detailed membrane-drug structural information can be gleaned from this method. The light collection/detection system can be a microscope or lense/collection optics can be built into a microfluidic chip or built into the instrumental reader (Raman/fluorescence).

These parameters can be manipulated so that the plasmonically enhanced signal monitored arises principally from the bilayer or from the cavity interior. Thus the bilayer itself can be monitored by metal (plasmonically and/or reflectance/Purcell effect) enhanced fluorescence or by surface enhanced Raman spectroscopy to study vibrational spectroscopy of drug-membrane binding or the cavity interior can be monitored to cavity to identify permeation of the molecule (marked by arrival SERS or fluorescence signal) and to elucidate dynamics of diffusion across the membrane as a function of membrane composition, (lipid composition, presence of proteins or transporters) molecular (or particle concentration) or environmental conditions (pH, ionic strength)

FIG. 1 illustrates the principle; The dynamics of transmembrane transport can be evaluated as a function of bilayer composition alongside structural interrogation of drug-membrane interaction/partitioning. To study dynamics of molecule (drug, particle polymer) by passive diffusion across the membrane, using gold nanocavity arrays and determination of the arrival time from of e.g. a drug administered to the proximal interface of the bilayer will be determined from the fluorescence or Raman enhancement emission intensity increase (or appearance) that arises as the species reaches the hot spot at the cavity interior after crossing the membrane. This provides a simple but quantitative indication of reagent permeation through the bilayer. Drug permeation/arrival time can be interrogated against various other conditions including drug concentration, pH, ionic gradient and the chemical composition of the membrane. The lipid bilayer membrane can be a simple single phospholipid species such as DOPC or more complex ternary or beyond with compositions that mimic true bilayers including inclusion of protein, and can be selected to mimic disease or specific physiological organelles or tissues or indeed species such as bacteria.

In addition to intensity data, changes to fluorescence of the species or Raman of species and/or bilayer can provide insights into the nature and extent of association of the species with the bilayer. Because the platforms are metal, these measurements can be combined with Electrochemcial data, e.g. electrochemical impedance spectroscopy, to evaluate the integrity of the bilayer at the outset of the experiment and on exposure to drug Furthermore, by plasmonically structuring the arrays we can yield dramatically improved S/N of signal to interrogate the molecule by SERS or through euse of surface enhanced resonance Raman spectroscopy (SERRS), where the excitation laser wavelength is matched to an electronic transition outstanding enhancement of Raman signature from non-luminescent species to can be investigated.

Plasmonic Substrates with and without additional plasmonic hotspots:

The substrates can be unmodified metal (gold, silver or combinations of metals) comprising only the cavity array that can be prepared by microsphere lithography, or through 3D printing mask or direct printing and metal deposition protocols.

Figure 3:
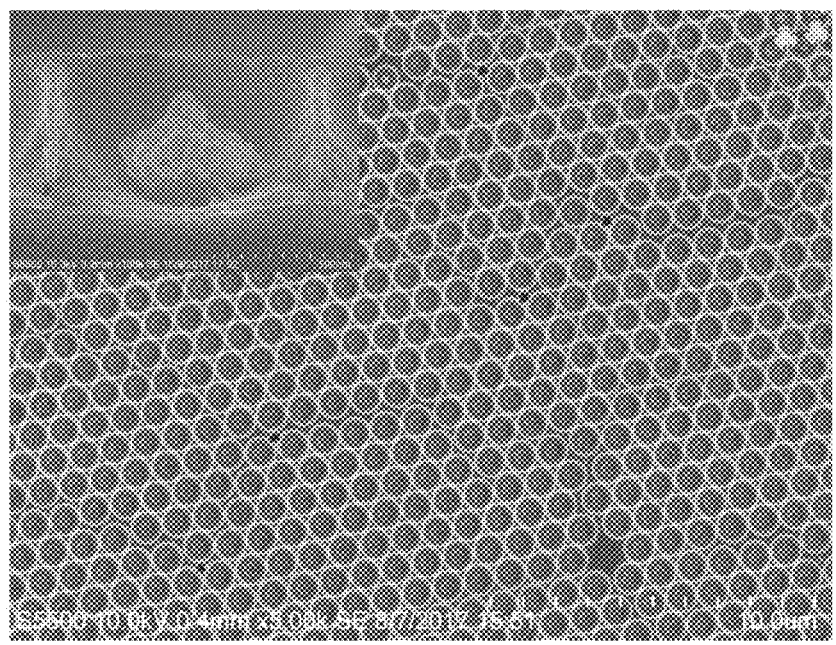
FIG. 3. HR-SEM of reactive ion etched nanoparticles within a 1 um diameter cavity array. The broad image shows the uniformity of the particles and array and the insert shows a side-on view of a single cavity showing the roughened pyramid shape of the etched particle. Raman signatures from these arrays show approximately 1000× enhancement compared to unmodified arrays.

Incorporation of additional plasmonic hot spots can be included in a hierarchical configuration, in which the strength and position of the plasmonic hot-spots can be prudently customized to suit the experiment requirements. For instance, one can employ direct photo-induced metal deposition to produce imprints of the plasmonic fields near the bottom of the cavity, thereby allowing for plasmonically-tagged drug arrival-time studies. Alternatively, one can also employ 3D-nanoprinting via 2-photon polymerization of photoresist (e.g. acrylate photoresist) to produce customized sub-nanostructure within the cavity. These nano-structures may be computationally designed via, for instance, using numerical methods to anticipate optical properties such as Finite Difference Domain (FDTD) method. inverse algorithm. Additional approaches to 3-D printing for addition of hot spots are described;
  (a) Plasmonic field induced polymerization/metal deposition-herein the plasmonic hots spot from the cavity array itself is used to deposit additional nanostructuring-through direct metal photodeposition where cavities are filled with a metal salt solution or where a polymer solution filled in the cavity and photoinduced cross-linking driven by the plasmonic field is used to create insoluble polymer structures that can be deposited over with metal vapour deposition following washing to create hot spots
  (b) Air bubble excluded zone nanoparticle prep (FIG. 2): Following filling by Fluorescence and SEM imaging of templated PDMS confirm that without sonication a small liquid unfilled region of the cavity is formed. We exploit this by, without sonication, filling Au cavity array pre-coated with C6 with an aqueous/ethanolic solution of surface active thiol. This blocks all but the region of the cavity where the air bubble is. Gold is then electrodeposited principally at the unmodified regions of the array to yield gold particles at the position of the air bubble in the well.
  (c) Fabrication of isolated Au-cavities with in-cavity nanostructures via reactive ion etching (RIF). In this approach, the cavities are prepared from electrodeposition of gold around PS sphere the spheres are then shrunk by RIF and a second (vapour) deposition is applied, this results in nano-flowers at the bottom of the well (FIG. 3). The resulting structures are highly uniform and the results once conditions of gold deposition are stable highly reproducible from batch to batch. Under normal incidence excitation/collection we obtain a highly reproducible enhancement of SERS signature from these substrates compared to substrates without the additional nanostructuring (FIG. 3).

Figure 6:
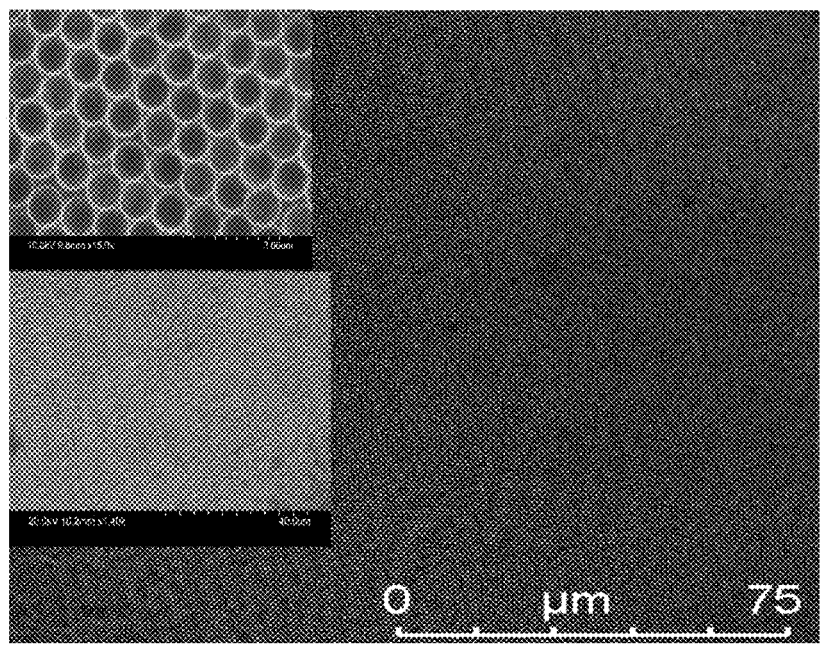
FIG. 6. Scanning electron microscopy (inset) and Confocal fluorescence microscopy images of 1 μm diameter gold cavity arrays, showing the extent of order over different length scales. The emission from the cavities reflects the intensity of light reflected from the cavity which is, in part, exploited for signal enhancement in this application.
Figure 7:
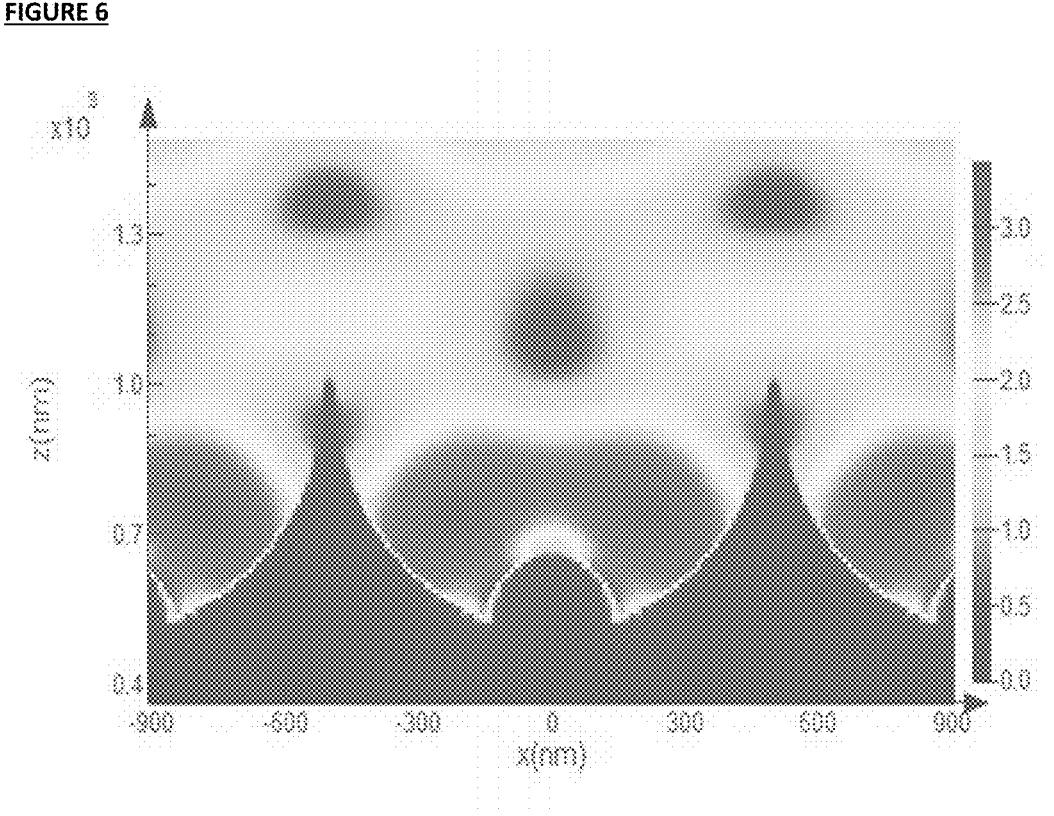
FIG. 7. Localized plasmonic fields created by (Left) in-cavity half-hemispheres, and (Right) randomized nano-pyramide.

The invention provides a unique approach to assessment of molecular membrane permeability which exploits the cavity nature (FIG. 6) of the arrays and their plasmonic fields (metallic structures). The assay utilizes the peak plasmonic fields within the nano/micro cavity to report the arrival of a drug after it transports across the cell membrane model based on Raman or emission signal from the molecule.

The assay itself is unique as drug-membrane molecular interactions and partitioning across porous arrays has not been reported by SERS previously and the dynamic monitoring drug transport across membrane suspended over a nanostructure using metal enhanced fluorescence/SERS/SERRS enhancement for arrival time measurement is not previously reported.

Figure 9:
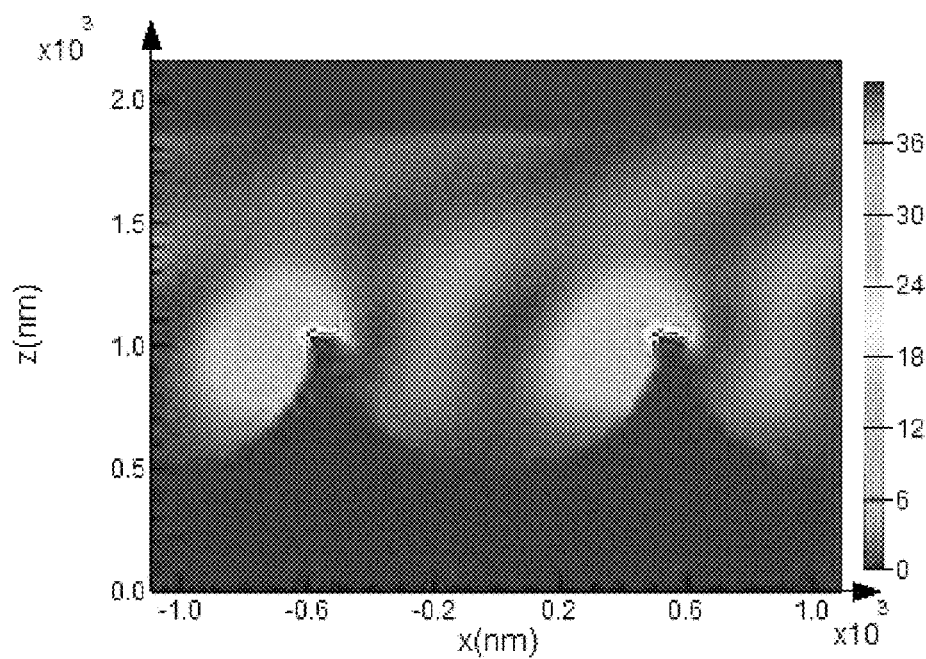
FIG. 9. Dynamic SERS response following permeation of Doxorubicin at DOPC bilayer suspended across PBS filled 1 μm diameter gold array. The—Doxorubicin was administered at 200 μl into the external contacting solution at the lipid bilayer. Raman Shifts in the lipid modes indicate drug binding and orientation at the bilayer and the appearance of drug vibrations as it reaches the hot spot (here the cavity aperture indicates permeation time).
Figure 9:
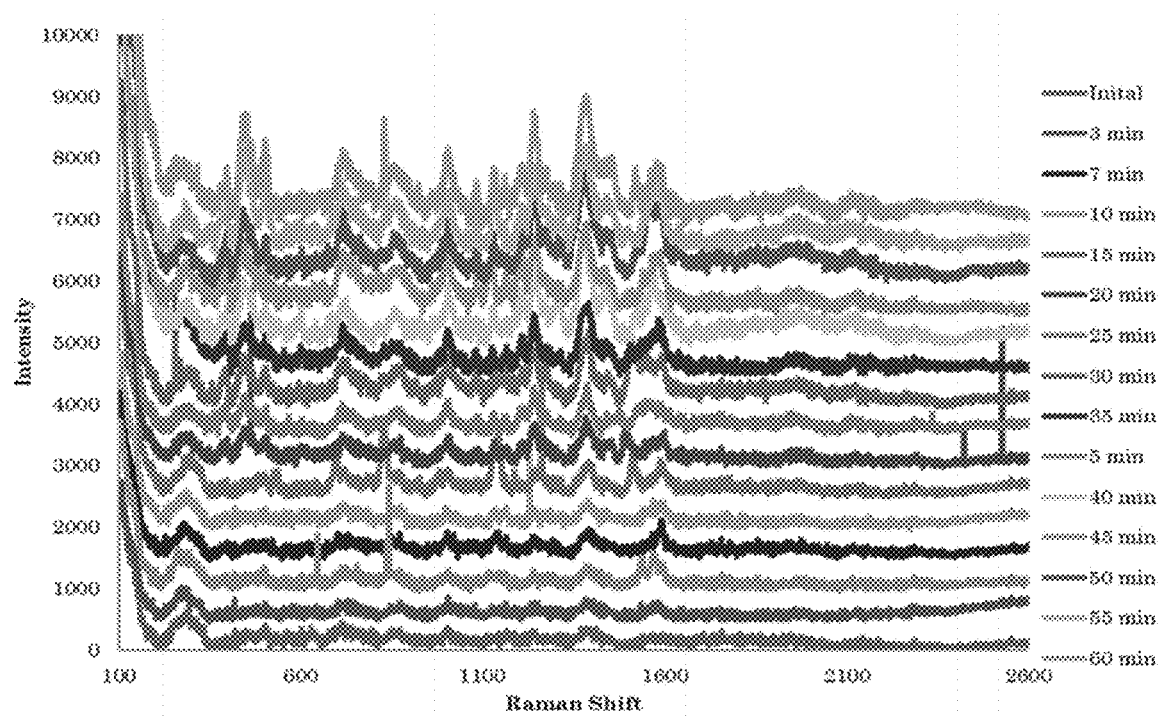

The use of plasmonic sub-nanostructures within the cavities to generate and enhance localized fields to detect arrival of a molecule after it crosses the membrane is unique. These structures can be prepared in a number of ways (as described above). Since the methods we use to develop sub-nanostructure growth within the nanocavieis is also highly ordered, we have arrays with enhanced optical properties but without compromising the reproducibility. FIG. 9 shows the FDTD-simulation results of cavities containing sub-nanostructures, illustrating the possibility of creating localized in-cavity plasmonic fields. The specific geometry of the cavity platform described here also permits modulation of the excitation fields to excite different plasmonic modes. For example, one can simply switch from in-cavity plasmonic fields to ring-plasmonic-mode around the mouth of the cavities by adjusting the illumination angle (see FIG. 10), allowing arrival-time study and membrane spectroscopy to be carried out with the same platform.

Figure 10:
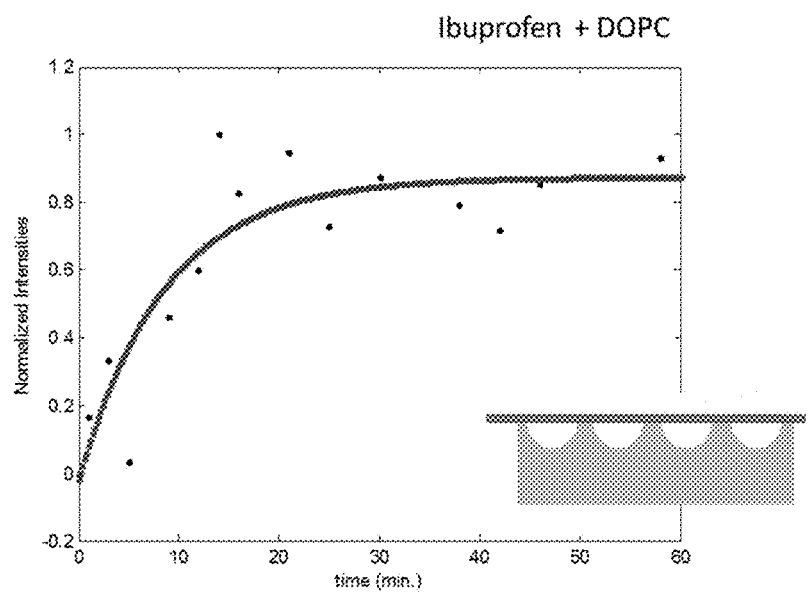
FIG. 10. Fitting of diffusion model (I(t)=I_max+(1_o−I_max)*exp(−kt)) to SERS response of Ibuprofen transporting across DOPC membrane suspended over 1 um Au cavity array measured at 785 nm. Normalized intensities were derived at the 1605 cm$^{-1}$ peak of ibuprofen.
Figure 11:
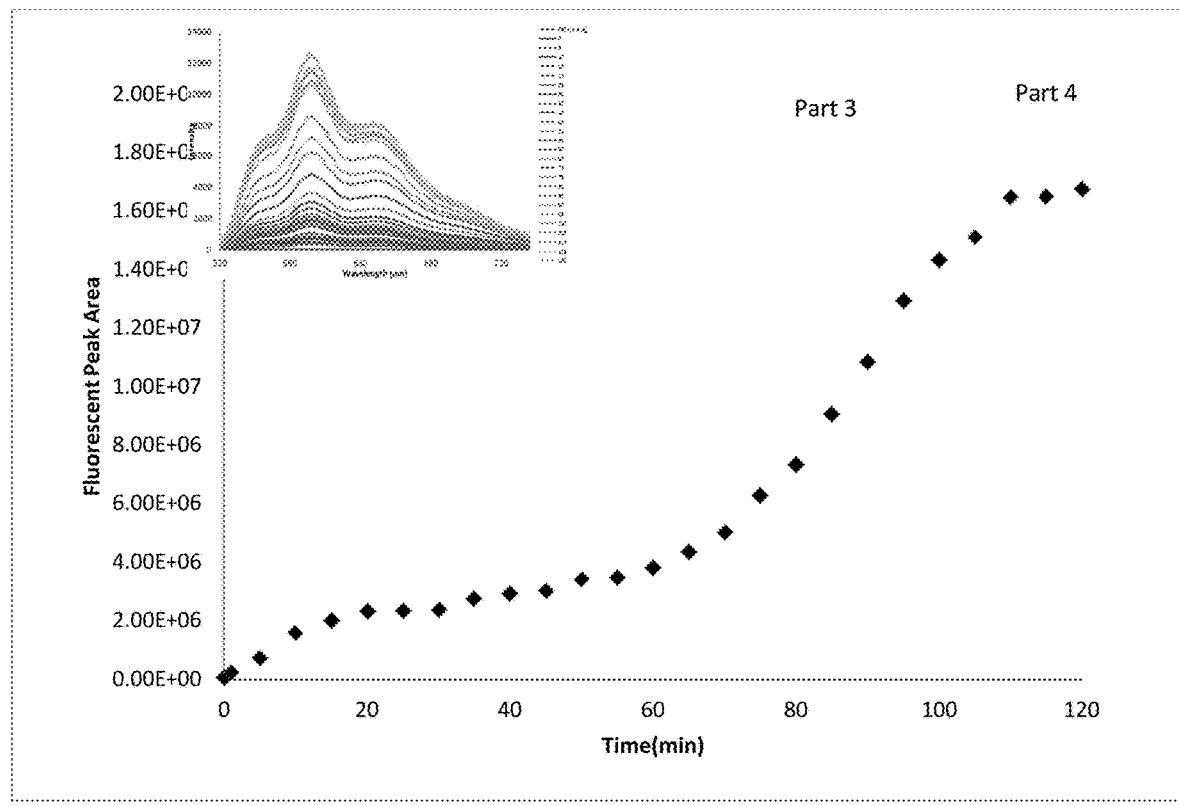
FIG. 11. 2-hour monitoring of fluorescent intensity as 0.1 mM of Doxorubicin administered to a DOPC bilayer spanned over 1 μm diameter gold array. Fluorescent peak area at 600 nm plotted vs time. Four separate patterns observed across a range of concentrations, where part 1) the modest rise is attributed to initial diffusion of drug into chosen buffer, Part 2) a slow increase in intensity attributed to the drug reaching and residing within the bilayer, Part 3) a dramatic increase in intensity due to the drug diffusing through the bilayer and reaching the enhancing properties of the cavity below. Part 4) equilibrium is reached shown by the plateau.

The present invention allows the kinetics of drug binding and permeation on conventional array substrates to be observed and monitored down to nanomolar concentrations with high signal-to-noise analysis of drug-membrane interactions. Thus, it is possible to access signal across a range of physiologically relevant concentrations (FIGS. 9, 10 and 11). Depending on the environmental sensitivity of the luminophore, its interaction with the bilayer may lead to modifications to the emissions spectrum. This was observed in the case of doxorubicin and duanorubicin both of whom show transitory shifts in emission peak maximum and relative intensity of the vibrational progression whilst in the bilayer. The solution spectrum is recovered when the drug reaches the well where greatest enhancement occurs and this dominates the spectral contributions, see for example FIG. 12.

Conversely, this assay can also distinguish between drugs that are permeable and non-permeable, for example in FIG. 13 a ternary lipid bilayer comprising DOPC:SM:Chol of 40:40:20% mol/mol was employed and as the figure shows the emission from two replicate measurements of 0.1 mM of the drug reaches as stead state after less than 20 mins, which corresponds to the time taken for the drug in the unstirred solution to distribute homogenously. The final intensity achieved for this drug when it reaches the cavity (either in the bare substrate or through a DOPC bilayer is roughly 2 orders of magnitude higher than the intensity observed here. This indicates the drug does not reach the cavity in the 2-hour window monitored here and we conclude that the ternary lipid composition, which is known to form extended liquid ordered domains is impermeable to the drug. Identical behaviour is observed at DOPC if we use an impermeable molecule such as Draq 7.

Materials and Methods
Array Preparation:
Conventional Array Preparation—without Nanostructuring:

Arrays were prepared using Gold wafer discs (AMS Biotechnology limited) consisting of a non-conductive silicon base, a 10 nm titanium layer for adhesion and a 100 nm gold layer, cut into approx 1.5×0.8 cm. The substrates were washed carefully with acetone, ethanol and water before drying under nitrogen. Substrates were then used directly or placed into the vacuum chamber of a Harrick PDC-002 plasma cleaner (Harrick Plasma) and were air-plasma treated during 5 minutes at a pressure of 1000 mTorr using high power setting (29.6 W applied to the RF coil).

The chips are mounted onto a holder and 20 µl of polystyrene spheres (Polysciences Inc.) (PS spheres solutions of 3 µm, 1 µm, 850, 700 and 510 nm diameter were purchased from Polysciences, Inc. and were respectively diluted to between 1 and 1.4% (% solid wt. in solution) in deionised water. 20 µL of the diluted solution was then drop casted onto the clean gold-silicon substrates before covering it with a clean microscope glass slide (Corning® Inc) at a contact angle of 2°) at 1% (w/v) solution was deposited onto the gold wafers. A glass slide was then placed over the chip causing a capillary effect. The mounted chips were placed onto a platform at an angle that encourages monolayer formation of the sphere. The chips were left to dry overnight at 4° C., the liquid evaporated fully, resulting in a thin layer of spheres across the chip. This was then examined under a light microscope to determine if multilayers occurred. A small area at the edge of the chip is then removed of spheres using tape.

Gold deposition was completed by immersing the sample in a gold salt solution (Technic inc) that was previously degassed with nitrogen for 15 minutes. Deposition was performed using a standard 3 electrode set up. The sample acts as the working electrode, while an Ag/AgCl is used as the reference electrode and a platinum wire as a counter electrode. Deposition conditions vary depending on the deposition solution, but typically a potential of −0.6 V was applied by an electrochemical workstation 990 CH instrument. When the optimal charge is reached the samples are then removed, rinsed with deionised water and left to dry.

Where selective top modification is required (i.e. prior to bilayer assembly) the array was left in contact with an ethanol or (80:20 ethanol water solution of 1 mM) of the deposition OH terminated thiol (typically 6-mercaptohexanol) overnight.

The spheres are then removed by immersing the cavity in Tetrahydrofuran (THF) and sonicating for 5 up to 30 minutes (the PS was confirmed gone by EIS and/or Raman spectroscopy) and the resulting substrates where then characterised by SEM.

Gold electrodeposition was then performed through the PS microspheres template using a potentiostat CH Instrument model 900 electrochemical workstation and an Elevate® gold 7990 salt solution from Technic Inc. USA. The solution was degassed by purging for 30 minutes with nitrogen. In the electrodeposition, the gold-silicon wafer was the working electrode, with a Ag/AgCl reference electrode and a platinum wire as counter electrode. Gold was then electrodeposited at an applied potential of −0.6 V until the equator of the PS spheres monolayer was reached, trapping them within the substrate. This characteristic point was easily controlled by monitoring the shape of the i-t curve.

The tape on the substrate was then peeled off and the sample was rinsed with deionised water to wash away any gold salt solution remaining.

Where needed control of the angle of sphere deposition or during gold deposition was achieved using a poly(methyl methacrylate) (PMMA) based platform was manufactured, on which six individual stages could be placed with a tilted front angle of 2° and a tilted side angle of 1°. Each stage can host a gold-silicon sample prepared as described previously which can be fixed to it using a double-sided tape.

The PMMA based platform holding the tilted stages was then put in a box with silica-gel to reduce the ambient moisture and substrates were left to dry overnight at a temperature of 4° C. Once the water fully evaporated, the gold-silicon substrates show an iridescent deposit indicative of a closed packed monolayer of dry PS spheres.

A tape with a circular hole of not more than 5 mm diameter was placed on the substrate, while ensuring that the hole was centred on a homogeneous iridescent area. A top band of the tape was then removed to allow connection with the potentiostat.

Fabrication of Nanostructures Using Plasma Etching.

Micro and nano PS beads half embedded in gold were physically modified using a dry etching method (adapted from Plettl et al. and Yang et al.). Substrates were place in the vacuum chamber of a Plasmalab 80 Plus Reactive Ion Etch System (Oxford Instruments) and were reacted in the oxygen plasma at a constant oxygen flow of 25 sccm and a chamber pressure of 50 mTorr. RF power applied varied from 50 W to 200 W and exposure time from 2 minutes up to 40 minutes depending on the size of the spheres to be etched and the size of the nano-particles to be obtained.

Following dry etching, substrates were sputter coated with gold using a sputter coater Model 108 from Agar scientific. After coating for 30 seconds at a current of 30 mA and a pressure of 0.08 mbar, substrates were then ready for characterisation (FIG. 1), chemical surface modification, SERS or Metal Enhanced Fluorescence (MEF) applications.

Nanostructured Pores Prepared Using the Exclusion Volume of Aqueous Filled Pores This approach is shown schematically in FIG. 19. Step 1 and 2 show the usual sphere gold deposition and modification of the top surface with thiol. Step 3 after the spheres are removed an ethanol/water solution containing thiol is then added to dried cavities without sonication and left for 8 hours. Step 4—the thiol has deposited everywhere except the excluded volume and in Step 5 after sonicating the gold deposition solution into the array a second electrodeposition is performed to assemble particles at the unmodified regions of the array.

The arrays were prepared as above, and after removal of the PS spheres and washing the arrays were dried under vacuum.

The arrays were then left in contact (without sonication or agitation) with a deposition solution of solution was soinicated in gently for 5 mins. The electrodeposition step was then repeated under conditions described above for varying times (typically approximately 30 to 50 seconds) and the resulting arrays were imaged by SEM as shown below. In general NPs were larger if gold deposition solution is sonicated into the array.

FIG. 20 shows nanoparticle modified arrays prepared from 3 um PS sphere assemblies after 30 seconds gold electrodeposition. (gold deposition left in contact with array left and middle) and after prior sonication of gold deposition solution Fabrication of Microarrays (Both with and without Nano-structuring) Using a 3-D Printed Master Mould Microarray fabrication process (FIG. 1) starts with the design and fabrication of negative master mould. The mould can be a simple hemispherical array or can incorporate nanostrucutres—including single nanostructures or pillars with varying gap at the bottom of the well: The design is performed applying SolidWorks software. The negative round cavities of different diameters, ranging from 1 till 3 μm, and different depths from 0.5 till 3 μm are designed. Initially hexagonally arranged cavities of 1 μm in diameter, depth ranging from 0.5 till 1 μm (step of the increment is 0.1 μm) and the distance between spheres of 0.2 μm, are designed. Subsequently, all the designs including all the dimensions are scaled up by 1.5, 2, 2.5 and 3 times.

Subsequent step is the fabrication of negative master mould. Nanoscribe 2-photon 3D printer is applied for this purpose, as it enables to fabricate the features of designed dimensions. Moreover, unlike most of lithographic techniques it allows to fabricate round shaped features. The master mould is printed from IP-Dip photoresist. The 3D printed part is sputter coated with 30 nm of gold.

The positive master mould is fabricated from Polydimethylsiloxane (PDMS). The SYLGARD® 184 PDMS prepolymer from Sigma Aldrich is prepared as follows: the base and curing agent are mixed in a ratio of 10:1 by mass respectively. Before casting of PDMS, 3D printed mould is nitrogen blown, in order to remove the dust and dirt from it. Mixed pre-polymer is casted onto negative 3D printed master mould and placed into desiccator for entrapped air removal. Subsequently, pre-polymer is placed in the oven (temperature 50° C.) for 12 hours, in order to be cured. The hardened positive PDMS part is demoulded.

The dual-cure off-stoichiometry thiol-ene polymer (OSTE+) OSTEMER 322 Crystal Clear by Mercene Labs is applied in the fabrication of negative microarray. Two OSTE+ constituents A and B are mixed by ratio 1.09 to 1. The PDMS mould is nitrogen blown for dust and dirt removal. The mixed pre-polymer is then casted onto the positive master mould from PDMS. In order to remove the entrapped air, the desiccation of pre-polymer is performed. The vacuum chamber is covered with aluminium foil, in order to protect the pre-polymer from light and therefore premature hardening during the desiccation. The desiccated part is then placed under the UV lamp (wavelength 365 nm) for 15 minutes. After the first hardening the demoulded polymer part is rubbery and contains the unreacted thiols and epoxies. The gold coating of 140 μm is then sputtered on top of the fabricated negative part. The final step is the second thermal curing (1 hour at 90° C.), during which all thiols and epoxies react, the polymer becomes stiff and the fabricated microarray (FIG. 2) due to epoxy interaction binds to the sputter coated gold.

Figure 4:
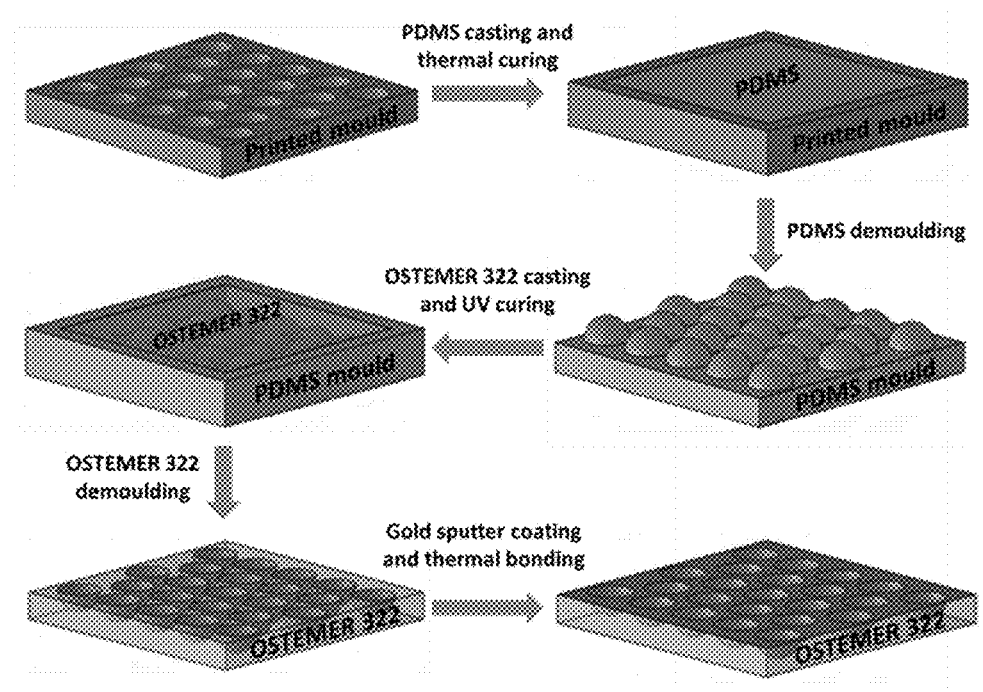
FIG. 4: Schematic showing steps in fabrication of negative master mould for polydimethylsiloxane (PDMS) casting.

Fabrication of Negative Master Mold for Polydimethylsiloxane (PDMS) Casting (FIG. 4).

The millimetre range arrays of negative SSVs are designed applying Computer Aided Design (CAD). Subsequently, the design is converted into STL format. DeScribe software is applied for scaling down the design to micrometre range (diameter 2 to 3 μm and depth 1 to 6 μm) and converting into compatible for 2 photon Photonic Professional GT 3D printer from NanoScribe GmbH. Consequently, negative master mould is printed on the Indium Tin Oxide (ITO) coated glass substrate (area 25×25 mm; height 0.7 mm) according to the design. IP-Dip photoresist is applied in the printing process.

2. Fabrication of Positive PDMS Master Mold.

Sylgard 184 from Sigma-Aldrich PDMS precursor in 10:1 base to curing agent ratio is mixed, degassed and casted onto 3D printed negative master mould, which is placed in the bath, following with additional desiccation (No visible entrapped air bubbles should be present). The part is thermally hardened at the temperature of 100° C. for 5 hours, gradually cooled down till room temperature and demoulded.

3. Sphere Segment Voids (SSVs) Substrate Fabrication

PDMS master mould is applied for transferring positive features on to the off-stoichiometry thiol-ene-epoxy (OSTE+) OSTEMER 322 Crystal Clear material from Mercene Labs. The material has a 40% off-stoichiometric ratio in between allyl and thiol functional groups. OSTE+ precursor is mixed by 1.09:1 A to B components ratio, degassed and casted over the positive PDMS mould. After casting additional degassing is performed, because during the casting air is entrapped, this could lead to inferior quality of the substrate. UV light (wavelength 365 nm) polymerisation for 20 minutes is performed, however this duration is dependent on the intensity of UV light. Part is constantly cooled during the UV curing, because UV curing generates the heat and therefore can initiate premature thermal hardening. UV-initiated radical polymerization results in a cross-linking network of the part of thiol and of all -ene groups in the allyls, therefore part of thiol functional groups and free monomers with epoxide functional groups remain unreacted. The UV cured part becomes rubbery, i.e. can be deformed and is surface modifiable. The part is demolded-negative SSVs are obtained. Subsequently 0.1 μm of gold is sputter coated on SSV substrate applying Agar Sputter Coater.

The part is thermally cured at the temperature of 110° C. (1 hour for every millimetre of the substrate thickness), in order to induce the reaction between unreacted excess of thiol groups and epoxies. The polymer hardens and due to epoxy chemistry creates a bond with a wide number of materials including gold. Polymer demonstrates complete inertness and decent barrier characteristics after thermal curing.

FIG. 5 shows the Raman enhancement achieved when the arrays are fabricated using this method:

Lipid Bilayer Assembly

For gold arrays, the assemblies were first modified with a OH terminated thiol (typically) 6-mercaptohexanol at the top surface by immersing the array in a ethanolic solution (1 mM) of the thiol for approx. 10 hours.

Following removal of PS spheres, if in place, washing and aqueous filling of the array a Langmuir monolayer of lipids was spread across the micropore array, using either a Model 102M, LB trough or Model KN2006 from KSV-NIMA technology, LB alternate. The lipid mixture (across single or diverse lipid compositions) was prepared in chloroform at a concentration of 1 mg/ml. 50 μL of this solution was suspended on the water sub-phase. Fifteen minutes were allocated for evaporation of the solvent, prior to lipid monolayer compression. The rate of compression was 30 cm2/min and a constant surface pressure of 32 mN/m was maintained during the transfer of a probe labelled lipid monolayer from the water-air interface to the aqueous filled microcavity array. During LB transfer, the rate of the dipper motion was 5 mm min-1 to ensure adequate transfer. The monolayer coated template was either incorporated into the flow chamber by sticking the edges of the gold to a microfluidic substrate or simply through which lipid vesicles (100 nm SUVs (see below) of the same or different composition were containing lipid probe were injected into the flow chamber where the spontaneously disrupt to form a free-spanning lipid bilayer. After 10 minutes, the flow chamber was flushed with 1 ml of 0.01 M PBS buffer to remove excess vesicles and to maintain the fluid above the bilayer.

For arrays with sub micron dimensioned pores direct disruption of SUV can be used without prior monolayer formation SUV preparation:

The dried lipid films were rehydrated in 1 ml of 0.01 M phosphate buffer saline (PBS), pH 7.4 or 0.02 mM Tris buffer, pH 5.25 and vortexed for a period of 30-60 seconds. Next, the lipid suspensions were extruded 11 times through a 100 nm polycarbonate filter using a mini-extruder (Avanti Polar Lipids) to form large unilamellar vesicles (LUV) and diluted to final concentration of 0.25 mg/ml.

Lipid bilayer assembly was confirmed by fluorescence imaging, obtaining the Raman (SERS spectrum of the bilayer and in particular by running EIS of the assembled film prior to running Raman/fluorescence assays.

Electrochemical Impedance Spectroscopy (EIS)

EIS was performed on a CH660A potentiostat (CH Instruments, Germany). A standard 3-electrode cell was employed which comprised of an Ag/AgCl reference electrode, a platinum auxiliary electrode and the gold microcavity array which constituted the working electrode. The EIS was measured over a frequency range of 1 MHz to 0.01 Hz with an AC modulation amplitude of 5 mV at a potential bias of 0 V (vs Ag/AgCl). All measurements were carried out in a glass cell (approximate volume of 20 ml) in contact with PBS buffer maintained at pH 7.4 or 20 mM Tris buffer at pH 5.25. The EIS of the aqueous filled microcavity array coated with the DOPC lipid bilayer was measured initially prior to addition of drugs to ensure signal stability and then titrate drug solutions into the glass cell containing buffer and the electrochemical impedance response of the lipid bilayer following drug introduction was measured for each concentration. Each measurement takes approximately 10 minutes and the measurements were carried out at room temperature (20° C.). The measured data were analysed using Z-View software using the fitting model (Scheme 1) to calculate the change in membrane resistivity and conductance.

Equivalent Circuit Model (ECM) for MSL

In order to extract the resistance and capacitance values for the MSLBs, the EIS data were fitted to the equivalent circuit model (ECM) shown in FIG. 16 which was described previously for the lipid bilayer modified microcavity array electrode. The circuit consists of the solution resistance (Rsol) in series with a resistor and a capacitor, which are in parallel and correspond to the electric and dielectric properties respectively of membrane deposited on the electrode surface (Rm, Cm). The ECM also contains an additional component to account for the resistance of the cavity arrays (Rarray), and the double layer capacitance (all). The data for the bare cavities and cavities upon treatment with ME were fitted with a Rsol(Rm||Cm), as at this stage, in the absence of the bilayer, the resistance and capacitance are expected to be uniform along the surface of the electrodes. A Constant Phase Elements (CPE) is used in the equivalent circuit instead of pure capacitors to account for surface defects on both the electrode surface and the lipid bilayer. The impedance of a CPE is given by $Z_{CPE}=Q-1(j\omega)-\alpha$ where Q is the magnitude of the capacitance of the CPE, w is the angular frequency, and a is a real number between 1 and 0 (the closer a gets to 1, the more ideal the capacitive behaviour of the CPE). As increasing concentrations of drugs were titrated into the contacting electrolyte solution, it is expected that Rsol values may change depending on the nature of the drug, e.g. where it carries a charge but everything else remains static. Both Ibu and Dic are negatively charged under the pH conditions used here. Rarray is not expected to vary within a sample as there are no changes occurring in this component of the electrical system. Cm and Rm are connected in parallel. The membrane acts as an impermeable and insulating medium in biological cells as both the intracellular and extracellular environments contain various concentrations of ionic salt solutions permitted by the membrane. Similarly, in the MSLB, there is an external and internal environment comprising PBS buffer separated by a semipermeable phospholipid bilayer. Essentially, this insulating bilayer is separating two ionic phases and is hence acting as a capacitor.

Drug Permeation Measurements

A Horiba Labram HR instrument was used for both Raman and fluorescence measurements using a 50× long distance magnification objective (Leica). The wavelengths were typically 473 nm and 785 nm were used for fluorescence measurements and Raman measurements respectively. The instrument was calibrated using silicon prior to use. Samples were placed either on a clean glass slide or if required to be immersed in liquid in a small clean glass petri dish or were in microfluidic format. The laser was focused using the camera and spectra were taken. Typically a 1% neutral density filter and 300 μm slit were used for fluorescence and no filter for Raman. The spectrometers grating was kept consistent at 600 XX.

For drug/molecular diffusion studies, drug solutions were prepared as stock solutions for introduction into the bilayer contacting solution dissolved in PBS or Tris buffer at concentrations that permitted final concentrations (on contact with the bilayer buffer) of 1 nM to several millimolar. Where drugs were particularly insoluble ethanol, methanol or DMSO could be used to pre-dissolve the drug to get it into buffer. In all cases final organic concentration was less than 0.5% (and controls using EIS confirmed this did not affect permeability). Drug diffusion samples were analysed by first obtaining a bilayer spectra while sample is immersed in PBS. Once obtained, known concentrations of drug were added to the PBS in the case of Fluorescence in an open chamber of 2 mL volume containing the bilayer modified substrate spectra or in the case of Raman spectra in a closed microfluidic structure. The Raman or Fluorescence spectrum of the bilayer was collected prior to addition of drug and then following drug addition (typically concentration ranges depended on the drug but we evaluated at, above and below administration and physiological concentrations. Typically, a measurement was collected every 5 to 10 minutes following administration and where required the sample as refocused using the white-light/reflectance image of the array pores/Raman of the bilayer. One SERS spectrum was acquired immediately before the drug was introduced into the channel. To limit any effects due to mass-transport diffusion, a total of volume about 2 ml was flowed through the microfluidics in order to equalise concentration gradient in the channel. This is accomplished within 1-min, after which time-series measurements commenced, and continued at 3-5 min interval for a period of 45-50 min. All collected spectra were background-corrected, and a dynamic curve was then plotted selecting a characteristic SERS peak for the sample which may also be normalised to a background peak such as that of silicon or buffer.

For both measurements the excitation line was kept at 1% OD to ensure that heat from the laser did not cause permeation. Accumulations/exposure times used for measurement depended on the sensitivity of the method to the drug.

Angle Dependent Raman Measurements:

For angle dependent measurements stages milled from Teflon with angle normal to the microscope stage ranging from 10 to 60° was used.

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:

1. A method of assaying permeation of a test molecule across a lipid bilayer that employs a microfluidic device comprising:
   a substrate having at least one concave microcavity defining an aperture and having a metallic surface, and a liquid disposed within the microcavity;
   a lipid bilayer suspended across the aperture; and
   a microfluidic channel containing a liquid disposed on top of the substrate in fluid communication with the lipid bilayer,
   in which the liquid in the microcavity is separated from the liquid in the microfluidic channel by the suspended lipid bilayer,
the method comprising the steps of:
   passing a liquid containing a test molecule across the microfluidic channel;
   monitoring the intensity of a Raman or fluorescent signal from the test molecule as it permeates across the lipid bilayer and into the liquid in the microcavity and arrives at a metal enhanced plasmonic field within the microcavity by plasmonically-enhanced Raman or fluorescent spectroscopy; and
   determining an arrival time of the test molecule in the liquid in the microcavity, wherein the arrival time is a period of time calculated from when the test molecule is administered at a proximal interface of the lipid bilayer until the test molecule reaches the metal enhanced plasmonic field within the microcavity.

2. The method according to claim 1, in which the monitoring step comprises plasmonically enhanced Raman spectroscopy.

3. The method according to claim 1, in which the monitoring step comprises surface enhanced Raman spectroscopy (SERS) that employs exciting light that is coincident with the plasmon of the metal.

4. The method according to claim 1, in which the monitoring step comprises surface enhanced resonance Raman spectroscopy (SERRS) that employs exciting light that is resonant with the absorption of the test molecule.

5. The method according to claim 1, in which the spectroscopy is metal enhanced fluorescent spectroscopy.

6. The method according to claim 1, in which the molecule is fluorescent or comprises a fluorescent label.

7. The method according to claim 1, in which the metallic surface of the microcavity comprises a metal sub-nanostructure having a sub-micro dimension configured to enhance a localised in-cavity plasmonic field.

8. The method according to claim 1, in which the metallic surface of the microcavity comprises a metal sub-nanostructure having a sub-micro dimension configured to enhance a localised in-cavity plasmonic field, in which the metal sub-nanostructure has a dimension of 5-200 nm.

9. The method according to claim 1, in which the metallic surface of the microcavity comprises a metal sub-nanostructure having a sub-micro dimension configured to enhance a localised in-cavity plasmonic field, wherein the monitoring step comprises SERS or SERRS and in which the excitation laser wavelength is matched to an electronic transition enhancement of Raman signature from non-luminescent species to be investigated.

10. The method according to claim 1, in which the metallic surface of the microcavity comprises a metal sub-nanostructure having a sub-micro dimension configured to enhance a localised in-cavity plasmonic field, in which the metal sub-nanostructure is fabricated by a method selected from the group consisting of: direct photo-induced metal deposition to produce imprints of the plasmonic fields; 3D-nanoprinting via 2-photon polymerization of photoresist; plasmonic field induced polymerization/metal deposition; air bubble excluded zone nanoparticle preparation; and reactive ion etching (RIF).

11. The method according to claim 10, in which the imprints of the plasmonic fields are near the bottom of the cavity.

12. The method according to claim 1, in which the test molecule is a drug.

13. The method according to claim 1, in which the metallic surface of the at least one microcavity is selected from gold, silver or an ostamer.

14. The method according to claim 1, in which the metal is gold, and in which a wavelength of an excitation line is configured to be coincident with the plasmonic absorption of the gold, or an excitation or an emission must be coincident with the energy of the plasmonic field for enhancement.

15. The method according to claim 1, in which the monitoring step further comprises calculating a residence time of the test molecule in the lipid bilayer as it permeates across the lipid bilayer.

16. The method according to claim 1, in which the method employs changing an angle of incident light during the monitoring step.

17. The method according to claim 1, in which the method comprises modulation of an excitation field to excite different plasmonic modes during the monitoring step.

18. The method according to claim 1, in which the method comprises monitoring residence time of the test molecule in the lipid bilayer at a first excitation or detection angle of incident light, and then altering the excitation or detection angle of incident light to monitor the arrival of the test molecule in the microcavity.

\* \* \* \* \*